United States Patent
Chen

(10) Patent No.: US 9,783,929 B2
(45) Date of Patent: Oct. 10, 2017

(54) DETERMINATION OF CD AND/OR MD VARIATIONS FROM SCANNING MEASUREMENTS OF A SHEET OF MATERIAL

(75) Inventor: Shih-Chin Chen, Dublin, OH (US)

(73) Assignee: ABB Schweiz AG, Baden (CH)

(*) Notice: Subject to any disclaimer, the term of this patent is extended or adjusted under 35 U.S.C. 154(b) by 1306 days.

(21) Appl. No.: 13/457,870

(22) Filed: Apr. 27, 2012

(65) Prior Publication Data

US 2012/0278032 A1 Nov. 1, 2012

Related U.S. Application Data

(60) Provisional application No. 61/480,249, filed on Apr. 28, 2011.

(51) Int. Cl.
*G06F 15/00* (2006.01)
*D21G 9/00* (2006.01)
(Continued)

(52) U.S. Cl.
CPC ........... *D21G 9/0009* (2013.01); *G01N 21/86* (2013.01); *G01N 33/346* (2013.01); *G01N 21/8901* (2013.01)

(58) Field of Classification Search
None
See application file for complete search history.

(56) References Cited

U.S. PATENT DOCUMENTS 4,150,313 A 4/1979 Panza
4,910,688 A * 3/1990 Amini .................... G01R 23/16
700/129

(Continued)

FOREIGN PATENT DOCUMENTS

EP 1665981 A1 6/2006
EP 1768108 A1 3/2007

OTHER PUBLICATIONS

Sabatucci, Arianna; International Search Report and Written Opinion; International Application No. PCT/US2012/035385; Oct. 19, 2012; European Patent Office.

(Continued)

*Primary Examiner* — Paul D Lee
*Assistant Examiner* — Mark Crohn
(74) *Attorney, Agent, or Firm* — Taft Stettinius & Hollister LLP

(57) ABSTRACT

CD variations and/or MD variations in scan measurements are determined from spectral components of power spectra of scan measurements taken using two or more scanning speeds. Dominant spectral components having the same spatial frequencies identify CD variations and dominant spectral components having the same temporal frequencies identify MD variations. Dominant spectral components are extracted from a noisy power spectrum (PS) by sorting all spectral components into an ordered PS. A first polynomial representing background noise of the ordered PS is used to set a first threshold. Spectral components of the ordered PS that exceed the first threshold are removed to form a noise PS. A second polynomial representing the noise PS is used to set a second threshold. Spectral components of the PS that exceed the second threshold are identified as dominant spectral components of the PS.

11 Claims, 21 Drawing Sheets

(51) Int. Cl.
*G01N 21/86* (2006.01)
*G01N 33/34* (2006.01)
*G01N 21/89* (2006.01)

(56) References Cited

U.S. PATENT DOCUMENTS

| | | | |
|---|---|---|---|
| 4,939,929 | A | 7/1990 | Östman |
| 4,947,684 | A | 8/1990 | Balakrishnan |
| 5,297,548 | A | 3/1994 | Pologe |
| 5,298,122 | A * | 3/1994 | Munch .............. D21F 7/06 162/11 |
| 5,400,258 | A | 3/1995 | He |
| 5,623,421 | A | 4/1997 | Savic |
| 5,893,055 | A * | 4/1999 | Chen .............. G01N 21/89 700/128 |
| 5,943,906 | A * | 8/1999 | Shakespeare ....... G01N 33/346 73/159 |
| 5,960,374 | A | 9/1999 | Lausier |
| 6,008,675 | A | 12/1999 | Handa |
| 6,050,948 | A | 4/2000 | Sasaki et al. |
| 6,233,495 | B1 | 5/2001 | Chen |
| 6,298,322 | B1 | 10/2001 | Lindemann |
| 6,441,900 | B1 | 8/2002 | Fujiyoshi |
| 6,567,720 | B1 | 5/2003 | Figiel |
| 7,117,030 | B2 | 10/2006 | Berenfeld et al. |
| 7,567,871 | B2 | 7/2009 | Rohde et al. |
| 2011/0082692 | A1 | 4/2011 | Lim et al. |

OTHER PUBLICATIONS

Spectral Density Estimation; Wikipedia; XP-002679604; http://web.archive.org/web/20080303134910/http://en.wikpedia.org; Feb. 25, 2008.

Danissen, Paulina; Invitation to Pay Additional Fees and Communication Relating to the Results of the Partial International Search; International Application No. PCT/US2012/035385; Aug. 3, 2012; European Patent Office.

Seyhan Nuyan, et al.; "Unbiased Estimation of Variability From Scanning Measurements"; Control Systems Conference; Sep. 15-17; Stockholm; 2010; pp. 140-147.

Johanna Ylisaari et al.; "Scanner Path as a Manipulative Variable for Optimal Control and Diagnostics of CD Variations"; Control Systems/Pan-Pacific Conference; 2008; pp. 81-86.

Shih-Chin Chen, "Full-Width Sheet Property Estimation From Scanning Measurements"; Control Systems '92 at Whistler BC Canada; Sep. 1992; 8 pages.

* cited by examiner

DETERMINATION OF CD AND/OR MD VARIATIONS FROM SCANNING MEASUREMENTS OF A SHEET OF MATERIAL

FIELD OF THE INVENTION

The invention of the present application discloses a system for the determination of cross-machine direction (CD) variations and/or machine direction (MD) variations within scan measurements taken on a sheet of material. The disclosed approach compares power spectra of measurements obtained using two or more scanning speeds with respect to spatial frequencies for CD variations and with respect to temporal frequencies for MD variations. The CD and MD variations are identified by matching dominant spectral components of power spectra of measurements taken at two or more scanning speeds with respect to spatial and temporal frequencies, respectively. The system will be described with reference to measuring properties of a web of paper as it is being manufactured for which it was developed and is initially being used. However, it will be apparent that it is applicable to the determination of CD and/or MD variations from measurements of a wide variety of sheet material where the sensor(s) and the web are moved perpendicular to one another so that the sheet material measurements are obtained by scanning.

BACKGROUND OF THE INVENTION

In a sheet-making process, such as the manufacture of paper, sheet properties are commonly measured with sensors mounted on a scanner. The scanner traverses across the forming sheet back and forth while the paper sheet is moving in the direction perpendicular to the scanner's motion. A partially broken-away perspective view of a scanning system 100 is shown in FIG. 1. A scanner 102 is moved along a supporting frame which includes two beams 104 positioned one above a web 106 of material to be scanned and one below the web 106. The scanner 102 includes first and second members or heads 108, 110 which are moved back-and-forth along the beams 104 to scan the web 106 in the cross-machine direction (CD) or transversely to the web's direction of movement during manufacture. The web 106 of material is moved in the machine direction (MD) or x direction as indicated by the x axis of a coordinate system shown in FIG. 1 and the cross direction is in the y direction. A gap 112 is formed between the first and second heads 108, 110 with the web 106 of material to be scanned passing through the gap 112 for the scanning operation.

The web is sampled by one or more sensors moving along the traversing path to produce a continuous measurement which is processed to form a scanning measurement of a sheet property across the width of the sheet which is referred to as a "scan measurement". Scan measurements consist of arrays of values that are accumulated over small CD widths called "databoxes" or over short periods of time called "time samples", either of which may sometimes be referred to as "slices". Ideally, the traversing paths are perfectly perpendicular to the machine direction and the variation of the entire sheet would be completely captured in a matrix where the MD variation is represented by the average of each scan measurement and the CD variation is represented by the shape of the scan measurement. In reality, the scan measurements obtained from a scanning sensor capture the sheet property variations along diagonal traversing paths. The measurement usually cannot be separated in MD and CD variations easily. The system of the present application enables MD and CD variations in sheet scan measurements to be quickly and effectively separated.

SUMMARY OF THE INVENTION

The system of the present application determines cross-machine direction (CD) variations and/or machine direction (MD) variations within scan measurements of a sheet of material being measured, for example a sheet of paper, based on spectral components of power spectra of scan measurements taken using two or more scanning speeds. Dominant spectral components having the same spatial frequencies are used to identify CD variations and dominant spectral components having the same temporal frequencies are used to identify MD variations.

In accordance with one aspect of the invention of the present application, a process for determining CD variations from scanning measurements made of a sheet of material comprises scanning at least one sensor over a sheet of material at a first scanning speed to generate first scan measurements. The first scan measurements are transformed into a first spatial power spectrum with respect to a first spatial frequency and first spatial dominant spectral components of the first spatial power spectrum are detected. At least one sensor is scanned over the sheet of material to be measured at a second scanning speed to generate second scan measurements. The second scan measurements are transformed into a second spatial power spectrum with respect to a second spatial frequency and second spatial dominant spectral components of the second spatial power spectrum are detected. CD spectral components of the scanning measurements are identified by determining at least one of the first spatial dominant spectral components that are at the same spatial frequency as at least one of the second spatial dominant spectral components.

The first spatial frequency of the process may be equal to the second spatial frequency.

The process may further comprise scanning at least one sensor over a sheet of material to be measured at a third scanning speed to generate third scan measurements. The third scan measurements are transformed into a third spatial power spectrum with respect to a third spatial frequency. Third spatial dominant spectral components of the third spatial power spectrum are detected. The CD spectral components of the scanning measurements are identified by determining at least one of the first spatial dominant spectral components that are at the same spatial frequency as at least one of the second spatial dominant spectral components and at least one of the third spatial dominant spectral components.

The CD variations within the scanning measurements can be constructed using inverse transformation of the CD spectral components. The step of detecting first spatial dominant spectral components of the first spatial power spectrum may comprise sorting all spectral components from the first spatial power spectrum in order of magnitude to form a first ordered spatial power spectrum. Background noise of the first ordered spatial power spectrum can be represent with a first polynomial. A first deviation threshold may be set with respect to the first polynomial and spectral components of the first ordered spatial power spectrum may be compared to the first deviation threshold. Spectral components of the first ordered spatial power spectrum that exceed said first deviation threshold are removed from the first ordered spatial power spectrum to form a first noise spatial power spectrum. The first noise spatial power spectrum in the first spatial power spectrum is represented by a second polynomial. A second deviation threshold is set with respect to the second polynomial and spectral components of the first spatial power spectrum that exceed the second deviation threshold are identified as first spatial dominant spectral components of the first spatial power spectrum. Commonly the first and second polynomials are low-order polynomials.

The step of detecting second spatial dominant spectral components of the second spatial power spectrum may comprise sorting all spectral components from the second spatial power spectrum in order of their magnitudes to form a second ordered spatial power spectrum. Background noise of the second ordered spatial power spectrum is represented by a third polynomial. A third deviation threshold is set with respect to the third polynomial and spectral components of the second ordered spatial power spectrum are compared to the third deviation threshold. Spectral components of the second ordered spatial power spectrum that exceed the third deviation threshold are removed from the second spatial power spectrum to form a second noise spatial power spectrum. The second noise spatial power spectrum is represented by a fourth polynomial and a fourth deviation threshold is set with respect to the fourth polynomial. Spectral components of the second spatial power spectrum that exceed the fourth deviation threshold are identified as second spatial dominant spectral components of the second spatial power spectrum.

The process may further comprise transforming the first scan measurements into a first temporal power spectrum with respect to a first temporal frequency. First temporal dominant spectral components of the first temporal power spectrum are detected and the second scan measurements are transformed into a second temporal power spectrum with respect to a second temporal frequency. Second temporal dominant spectral components of the second temporal power spectrum are detected and MD spectral components of the scanning measurements are identified by determining at least one of the first temporal dominant spectral components that is at the same temporal frequency as at least one of the second temporal dominant spectral components. The process may further comprise constructing the CD variations within the scanning measurements by inverse transformation of the CD spectral components, and constructing the MD variations within the scanning measurements by inverse transformation of the MD spectral components.

In accordance with another aspect of the invention of the present application, a process for determining MD variations from scanning measurements made of a sheet of material may comprise scanning at least one sensor over a sheet of material to be measured at a first scanning speed to generate first scan measurements. The first scan measurements are transformed into a first temporal power spectrum with respect to a first temporal frequency and first temporal dominant spectral components of the first temporal power spectrum are detected. At least one sensor is scanned over the sheet of material to be measured at a second scanning speed to generate second scan measurements. The second scan measurements are transformed into second temporal power spectrum with respect to a second temporal scanning frequency. Second dominant spectral components of the second temporal power spectrum are detected. The MD spectral components of the scanning measurements are identified by determining at least one of the first temporal dominant spectral components that is at the same temporal frequency as at least one of the second temporal dominant spectral components.

The process may further comprise constructing the MD variations within the scanning measurements by inverse transformation of the MD spectral components. The process may further comprise transforming the first scan measurements into a first spatial power spectrum with respect to a first spatial frequency; detecting first spatial dominant spectral components of the first spatial power spectrum; transforming the second scan measurements into a second spatial power spectrum with respect to a second spatial frequency; detecting second spatial dominant spectral components of the second spatial power spectrum; and identifying CD spectral components of the scanning measurements by determining at least one of the first spatial dominant spectral components that is at the same spatial frequency as at least one of the second spatial dominant spectral components.

The process may further comprise constructing the MD variations within said scanning measurements by inverse transforming the MD spectral components; and constructing the CD variations within the scanning measurements by inverse transformation of the CD spectral components.

In accordance with an additional aspect of the invention of the present application, a process for extracting dominant spectral components from a power spectrum of noisy measurements may comprise sorting all spectral components from a power spectrum in order of magnitude to form a first ordered power spectrum; representing background noise of the ordered power spectrum with a first polynomial; setting a first threshold with respect to the first polynomial; comparing spectral components of the ordered power spectrum to the first threshold; removing spectral components of the power spectrum that exceed the first threshold from the ordered power spectrum to form a noise power spectrum; representing the noise power spectrum in the power spectrum with a second polynomial; setting a second threshold with respect to the second polynomial; and, identifying spectral components of the power spectrum that exceed the second threshold as dominant spectral components of the power spectrum. The first and second polynomials may be low-order polynomials.

BRIEF DESCRIPTION OF THE DRAWINGS

The benefits and advantages of the invention of the present application will become apparent to those skilled in the art to which the invention relates from the subsequent description of the illustrated embodiments and the appended claims, taken in conjunction with the accompanying drawings, in which:

FIG. 16($b$) illustrates the derived power spectrum of the measurement of FIG. 16($a$);

FIG. 17($b$) illustrates the derived power spectrum of the measurement of FIG. 17($a$);

DETAILED DESCRIPTION OF THE INVENTION

Figure 1:
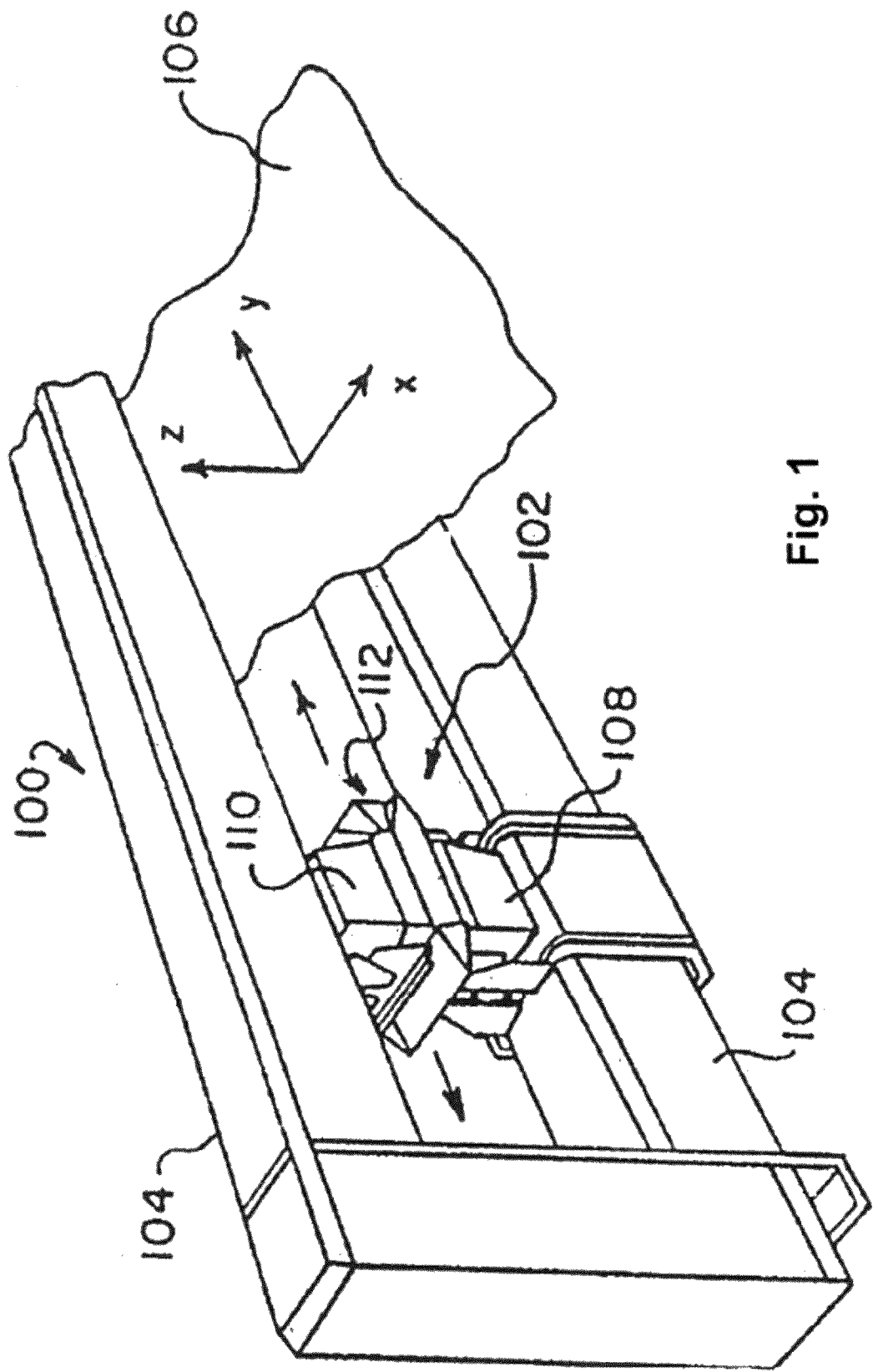
FIG. 1 is partially broken-away perspective view of a scanning system.

The system of the present application will be described with reference to measuring properties of a web of paper as it is being manufactured for which it was developed and is initially being used. In this regard, the system can be used to measure properties not only of sheet-making processes but also rewinding processes, coating machines, and many other similar processes and machines where scan measurements are commonly made. In addition, the system of the present application can be used for analysis of measurements that are obtained by generally perpendicular relative movement between a sheet of material to be measured and one or more sensors however that movement is affected. The disclosed system effectively separates the MD and/or CD variations in scan measurements. Since the separated MD and/or CD variations are more accurate than those determined by known prior art systems, the separated variations can be used as inputs to corresponding MD and/or CD controllers to better control processes being measured. The frequencies of the separated MD and/or CD variations can also be used to determine the root causes of the variations. Reconstructed MD and/or CD variation patterns, which might not be recognized directly from the scanning measurements, are useful tools in determining potential improvements if the identified variations are eliminated or substantially reduced.

Since scanning sensors have been used online to measure sheet properties for many years, it is understood that the scan measurements obtained from the zigzag path of the sensors mixes MD, CD and localized variations together. The separation of MD and CD variations from a scan measurement has always been a challenge. Traditionally, the MD variation component has been approximated by averaging the scan measurements and the CD variation component has been estimated by filtering subsequent scans at each databox. The approximated MD variation component would not contain any MD variations that are faster than the scan time and the approximated CD variation component is likely to be contaminated or distorted by those faster MD variations.

Several approaches have been used to overcome the challenge of separating MD variations and CD variations from scan measurements. As a first approach, scanning has been eliminated all together by using full-width, non-scanning measurement systems, see for example U.S. Pat. No. 5,563,809. In principle, this is an ideal solution. However, the cost and complexity of non-scanning measuring systems often out-weights the benefits that are expected to be gained from such systems. A few non-scanning systems have been designed in the past, but for the most part, they were not commercially accepted.

A second approach has been to scan faster, scan local regions, or mix scanning with single point measurements. These approaches shift the variation contents to be detected depending on the scan speed, the regions or the single points that are scanned. However, the fundamental challenge remains the same.

A third approach has been to process MD and CD separation more frequently, for example every 5 seconds instead of every 20-30 seconds in accordance with typical scan times. This approach of using more frequent processing of scan measurement data provides estimates of MD variations that are faster than the scan time thus improving the separation of MD and CD variation components. Unfortunately, such time-based estimation improvements still cannot detect MD variations that are shorter than the sampling time, such as 5 seconds.

The system for determination of CD and/or MD variations from scanning measurements of a sheet of material of the present application addresses the challenge of separating MD variations and CD variations from scan measurements and avoids the shortcomings of existing approaches. The scan measurement obtained from a scanning sensor can be transformed into the spectral domain by the well-known Fourier transformation technique implemented using a Fast Fourier Transform (FFT) algorithm or a Discrete Fourier Transform (DFT) algorithm. A wide variety of programs are commercially available for performing FFT and DFT, accordingly they will not be described further herein.

When scan measurements are taken over small CD widths, i.e., "databoxes", and hence expressed in databox resolution, the spatial (CD) frequency is derived from the databox resolution directly and the temporal (MD) frequency is obtained from the spectral frequency and the scan speed. For example, assuming a constant scan speed, the spatial frequency of a scan measurement that records its values in 600 databoxes across the width of the sheet, the spatial frequency ranges between 0.001667 and 0.50 (1/databox). On the other hand, the temporal (MD) frequencies of the same measurement are derived by multiplying the spatial frequencies with the scan speed. For example, the temporal frequency of a scan measurement obtained with a 30 databoxes/sec scan speed and a resolution of 600 databoxes ranges between 30·0.001667=0.05 Hz and 30·0.5=15 Hz.

Alternatively, when scan measurements are taken over short periods of time, i.e., "time samples", the temporal (MD) frequency is derived directly and the spatial (CD) frequency is obtained from the temporal frequency and the scan speed. For example, the temporal frequency of a scan measurement that is expressed in 1 millisecond time samples with a 20 second scan time at a constant scan speed, ranges between 0.05 Hz and 500 Hz. The spatial (CD) frequencies of the same measurement are obtained by dividing the temporal frequencies with the scan speed, for example 30 databoxes/sec. The spatial frequency of the same scan measurement ranges between 0.05/30=0.001667 and 500/30=16.67 (1/databox).

For a sheet of material that consists of persistent CD variations (pure CD variations), dominant spectral components in the CD direction with respect to their spatial frequencies will not change for different scanning speeds so that scan measurements taken at two or more different scanning speeds should yield the same dominant spatial spectral components. By comparing the spatial spectral content of scan measurements taken at two or more scan speeds, dominant spatial spectral components from the different scan measurements will be found at the same spatial frequencies. This overlap of the dominant spatial spectral components represents the CD spectral contents. Accordingly, using the system of the present application, the CD spectral contents in scan measurements can be identified and separated from the scan measurements.

On the other hand, for a sheet of material that consists of persistent MD variations (pure MD variations), dominant spectral components of MD variations obtained by scanning the sheet at two or more scanning speeds are not aligned with respect to the same spatial frequencies. However, when the spectral contents of scan measurements are shown with respect to their temporal frequencies, the dominant temporal spectral components will appear at the same temporal frequencies regardless of the scan speed. By comparing the spectral contents of scan measurements made at two or more scanning speeds with respect to temporal frequencies, the overlap of the dominant temporal spectral contents can be detected. Accordingly, using the system of the present application, the MD spectral contents in scan measurements can be identified and separated from the scan measurements.

After both MD and CD dominant spectral contents and their spatial and temporal frequencies are identified, inverse transformation, including, for example, the inverse Fourier transformation, can be used to separate MD and CD variation components from each scan measurement. The MD and CD dominant spectral components and their spatial and temporal frequencies can be identified regularly, intermittently, or on an event-driven basis while the separation of MD and CD variations from each scan measurement can be performed as frequently as needed to achieve optimal performance of the process that is being measured. The MD and CD dominant spectral components and their spatial and temporal frequencies can be identified for the full width of sheet or any portion of sheet while the separation of MD and CD variations from each scan measurement can also be performed accordingly to meet the needs of the associated control and/or diagnostic applications.

An example of a series of operations that can be performed for operation of the system of the present application will now be described followed by simulated examples illustrating the basic principles used in the present application to ensure complete understanding of operation of the system of the present application.

Figure 2:
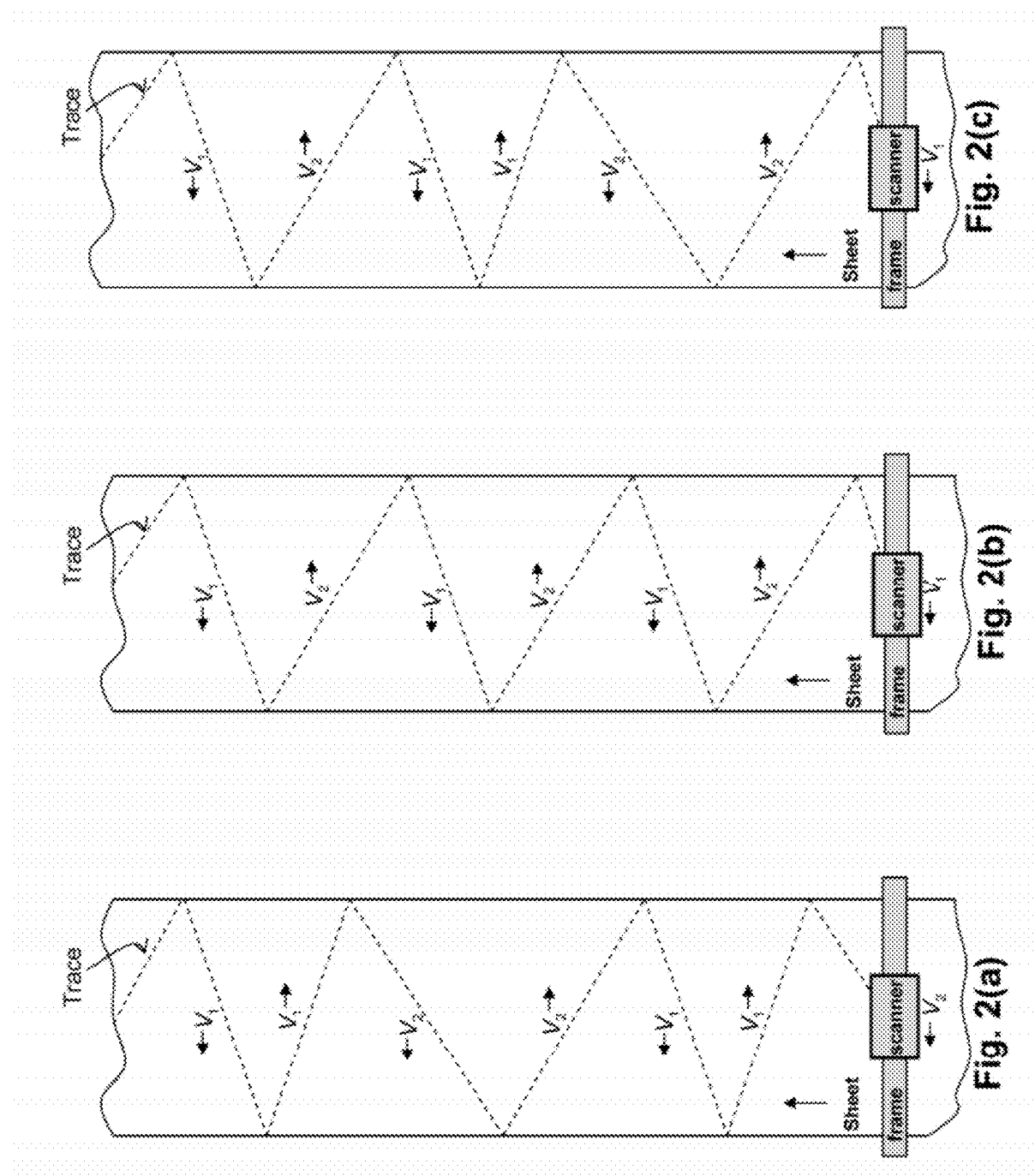
FIG. 2(a)-FIG. 2(c) show illustrative scanning speed patterns for use of two different scanning speeds of a scanning system.
Figure 3:
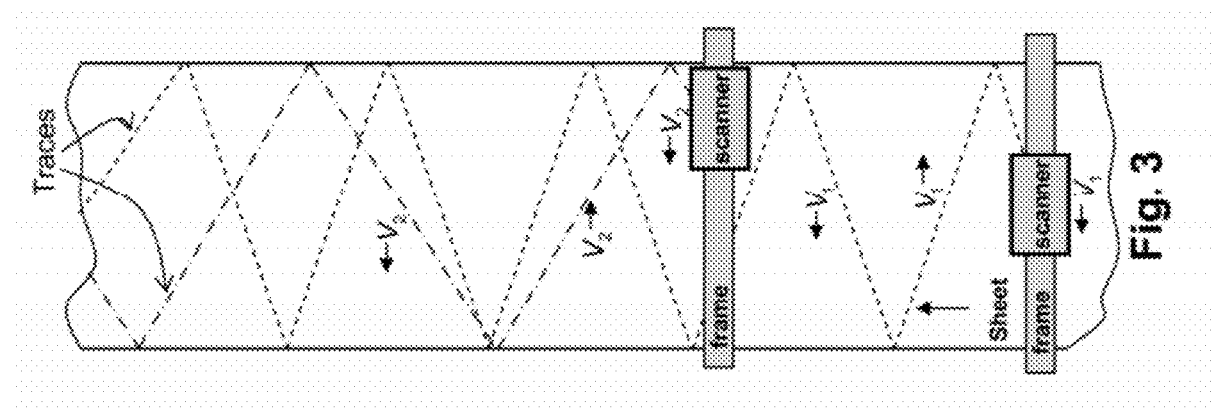
FIG. 3 shows the use of two scanning systems operating at two different scanning speeds.

1. Scan at least one sensor over a moving sheet with at least two scanning speeds which can be interleaved periodically, arranged by groups or can be event driven. FIG. 2 (a) illustrates groups of different scanning speeds showing two scans at a scanning speed of $V_1$ interleaved with two scans at a scanning speed of $V_2$. FIG. 2(b) illustrates alternating scans of different scanning speeds showing alternating scans at $V_1$ and $V_2$ scanning speeds. FIG. 2(c) illustrates random alternation of scanning speeds. Other arrangements for scanning with at least two scanning speeds will be apparent to those skilled in the art. For example two separate scanners, one scanning at a scan speed of $V_1$ and one scanning at a scan speed of $V_2$ are shown in FIG. 3. Thus, while the system of the present application is described with reference to a single scanner that is scanned at two scanning speeds, a single scanner that scans at more than two scanning speeds can be used. Also two or more scanners can be used with each scanner having similar sensors and scanning at one, two or more than two scanning speeds.

2. Scan measurements from the scanning sensor(s) and their corresponding scan speeds can be recorded as needed for processing scan measurements.

3. The scan measurements are transformed to their corresponding power spectra using, for example, Fourier transformation.

4. Dominant spectral components are detected from the transformed power spectra and their frequencies noted. Spatial (CD) frequency is based on the databox resolutions of the scanning operations and temporal (MD) frequency is based on the temporal sampling frequencies and the scan speeds of the scanning operations. A novel process for the extraction of dominant spectral components from noisy measurements will be described below.

5. The power spectra of the scan measurements at the different scan speeds are compared against their spatial frequencies or overlaid to identify the dominant spectral components that appear at the same spatial frequencies in both scan measurements to identify the CD spectral components.

6. The CD variations can be constructed using inverse transformation, for example, inverse Fourier transformation, of the identified CD spectral components.

7. The power spectra of the scan measurements at the different scan speeds are compared against their corresponding temporal frequencies or overlaid to identify the dominant spectral components that appear at the same temporal frequencies in both scans to identify the MD spectral components 8. The MD variations can be constructed using inverse transformation, for example, inverse Fourier transformation, of the identified MD spectral components.

9. The residual variations can be derived as the remainder after both the MD and CD variations are separated from each measurement.

Figure 4:
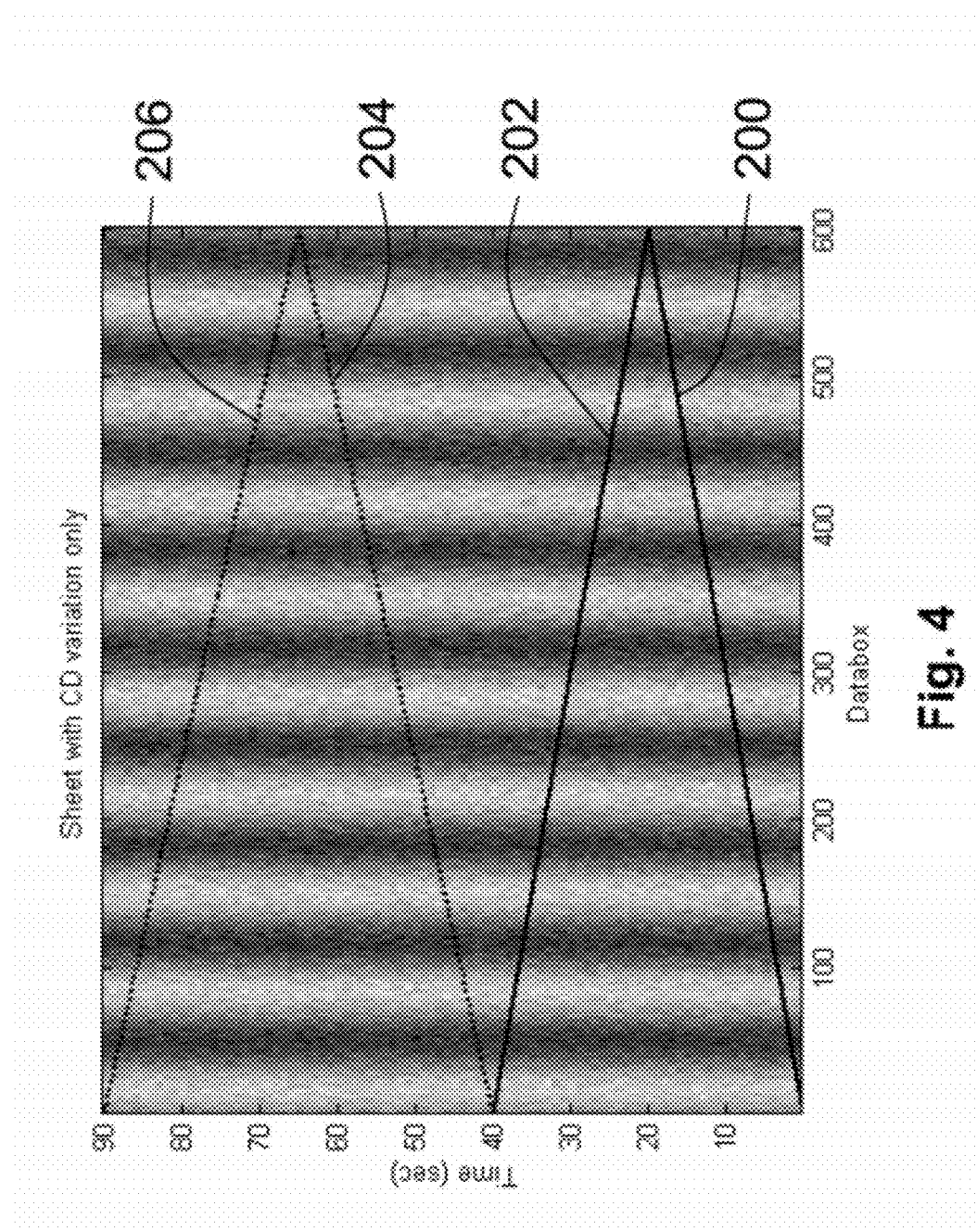
FIG. 4 shows a simulated sheet of material with CD variations only and the traces of four scans made at two different scan speeds on the simulated sheet.

The first simulated example is one where the sheet has only CD variations and two different scan speeds are used (20 second scans and 25 second scans—for 600 databox spatial resolution, these scan speeds correspond to 30 databoxes/sec and 24 databoxes/sec, respectively). A sheet with CD variations only and the traces of scans made using two scan speeds are shown in FIG. 4. The trace of each scan speed is marked with a diagonal line—the bottom or first two scans 200, 202 (solid lines) are 20 second scans, and the two top or last scans 204, 206 (dotted lines) are 25 second scans.

Figure 5:
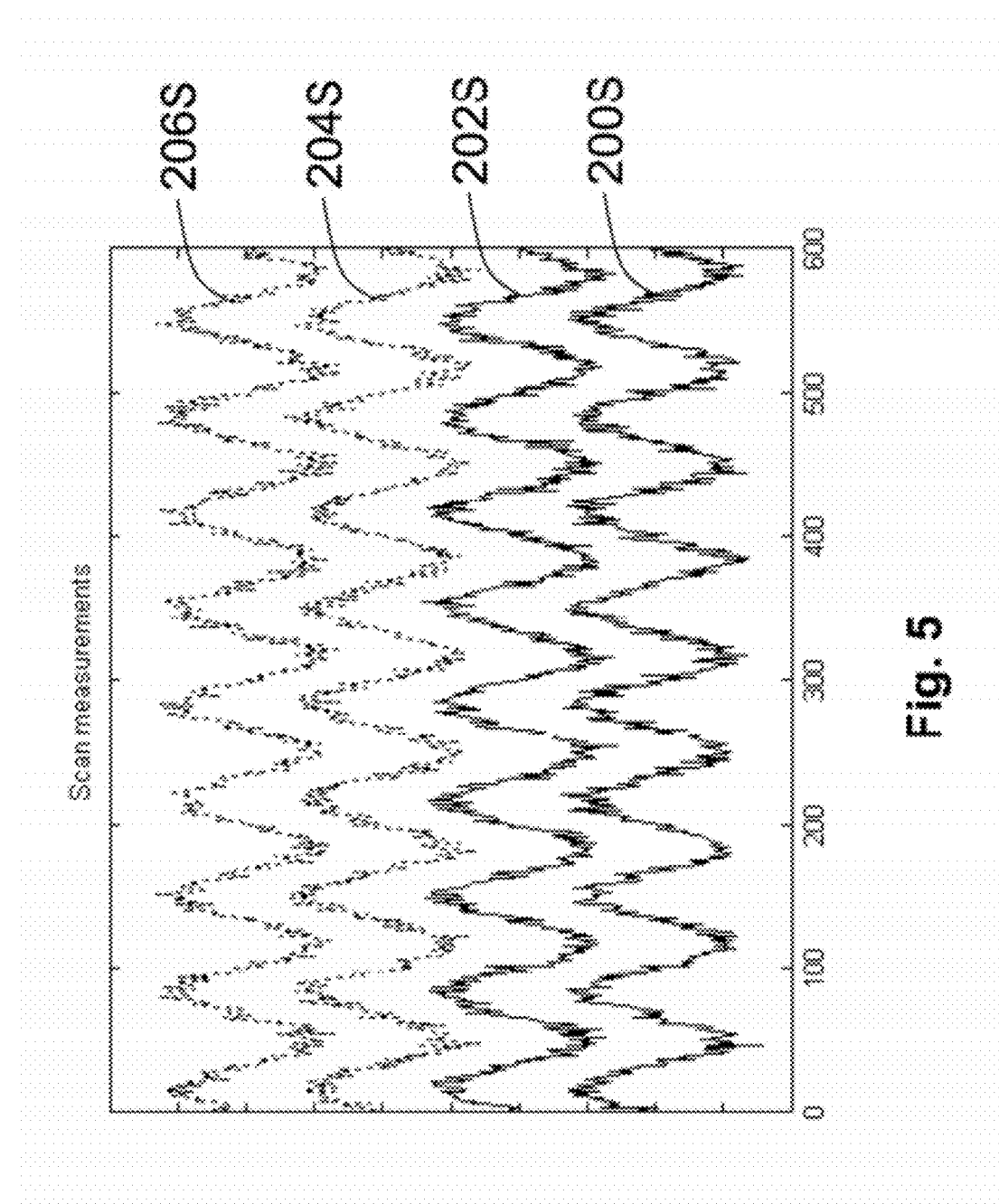
FIG. 5 shows scan measurements of the simulated sheet of FIG. 4 obtained using the scans shown in FIG. 4 having two different scan speeds.
Figure 6:
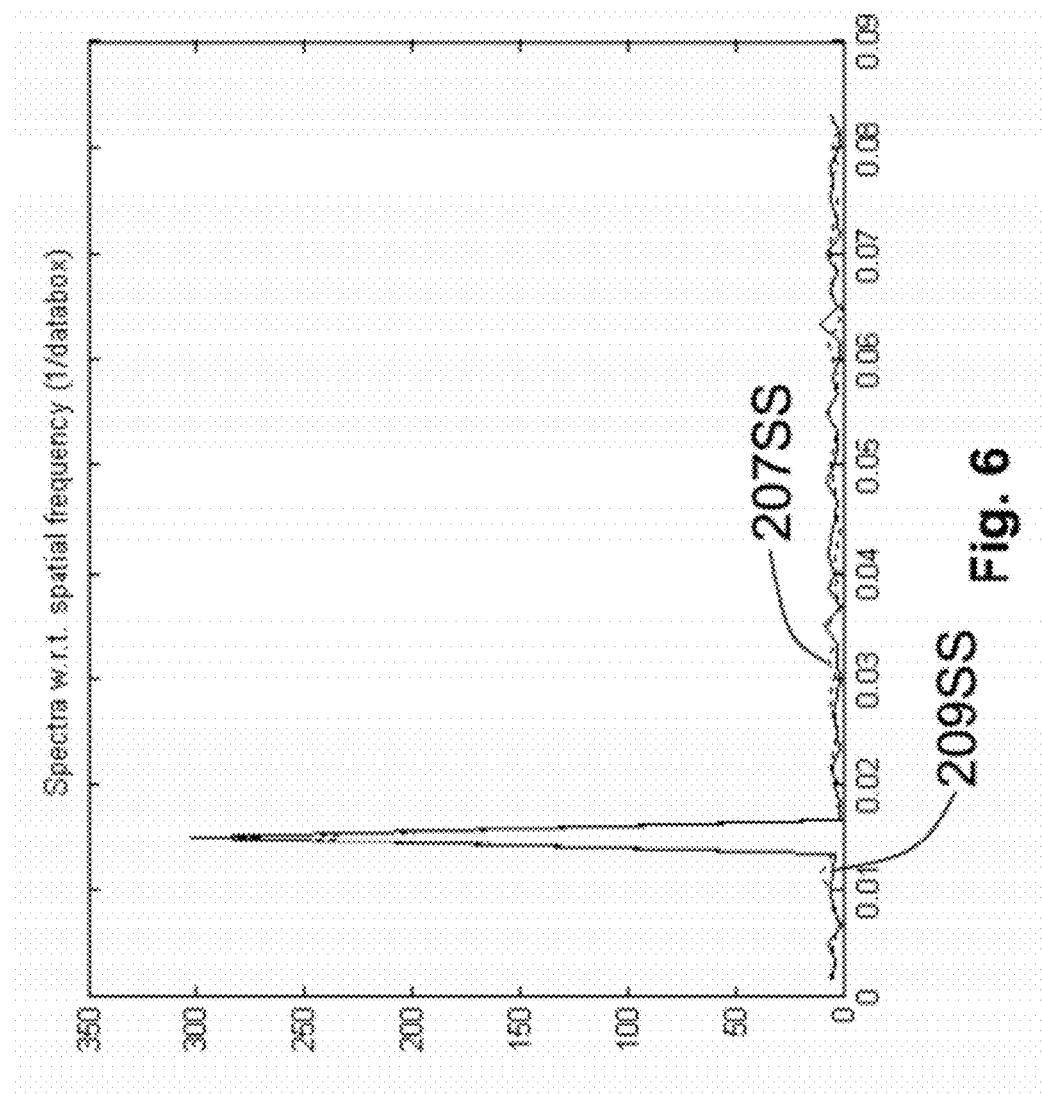
FIG. 6 is the spatial spectra of the scan measurements of FIG. 5.

Scan measurements 200S, 202S (shown as solid lines) and 204S, 206S (shown as dotted lines) obtained from FIG. 4 with two different scan speeds and their spatial spectra are plotted in FIG. 5 and FIG. 6, respectively. The dominant CD spectral components 207SS, 209SS, shown as solid and dotted lines, respectively, from the spectra appear at the same spatial frequency of 0.015 (1/databox).

Figure 7:
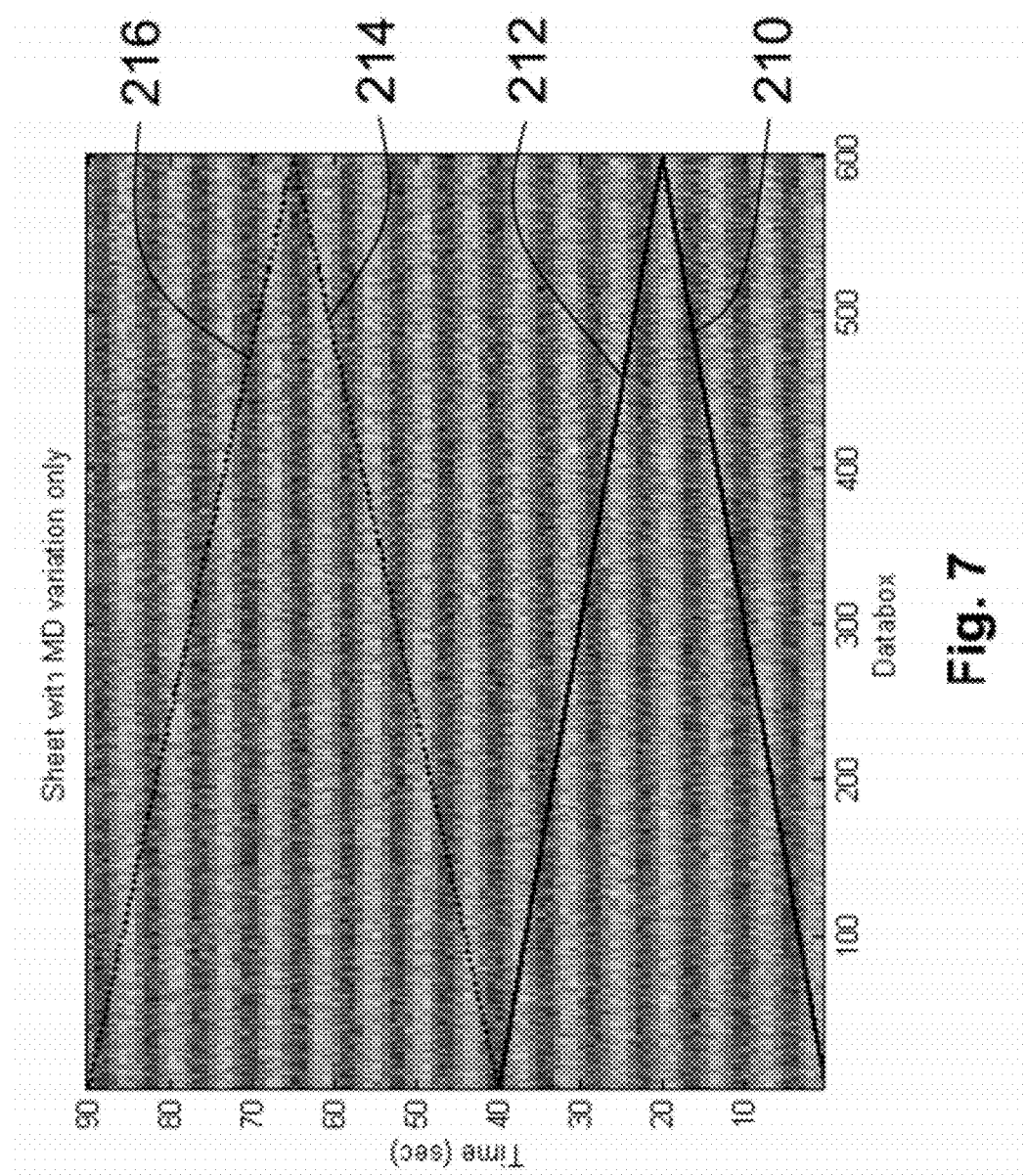
FIG. 7 shows a simulated sheet of material with MD variations only and the traces of four scans made at two different scan speeds on the simulated sheet.

The second simulated example is one where the sheet has only MD variations and again two different scan speeds are used (20 second scans and 25 second scans—for 600 databox spatial resolution, these scan speeds correspond to 30 databoxes/sec and 24 databoxes/sec, respectively). A sheet with MD variations only and the traces of scans made using two scan speeds are shown in FIG. 7. The trace of each scan speed is marked with a diagonal line—the bottom or first two scans 210, 212 (solid lines) are 20 second scans and the top or last two scans 214, 216 (dotted lines) are 25 second scans.

Figure 8:
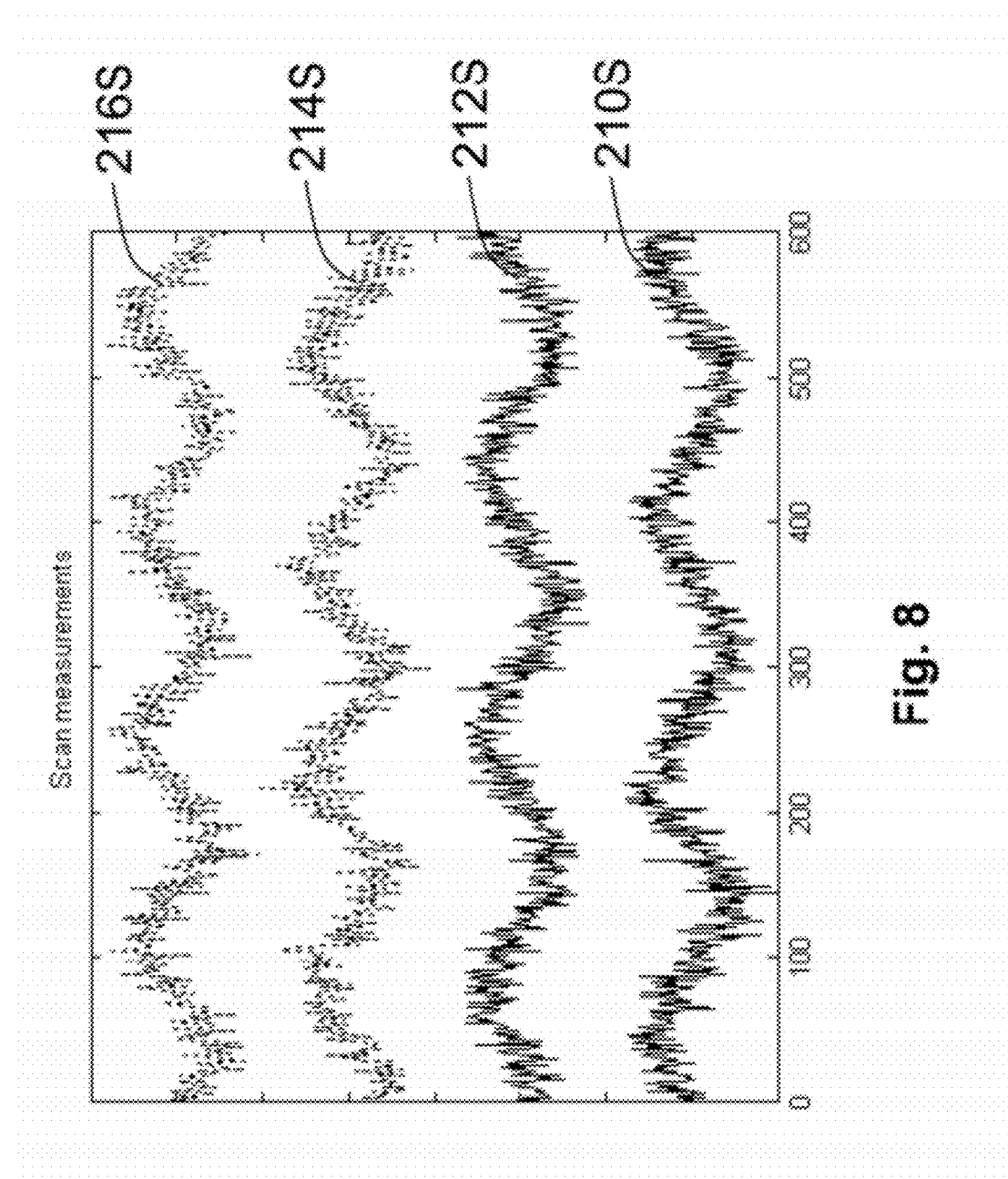
FIG. 8 shows scan measurements of the simulated sheet of FIG. 7 obtained using the scans shown in FIG. 7 having two different scan speeds.
Figure 9:
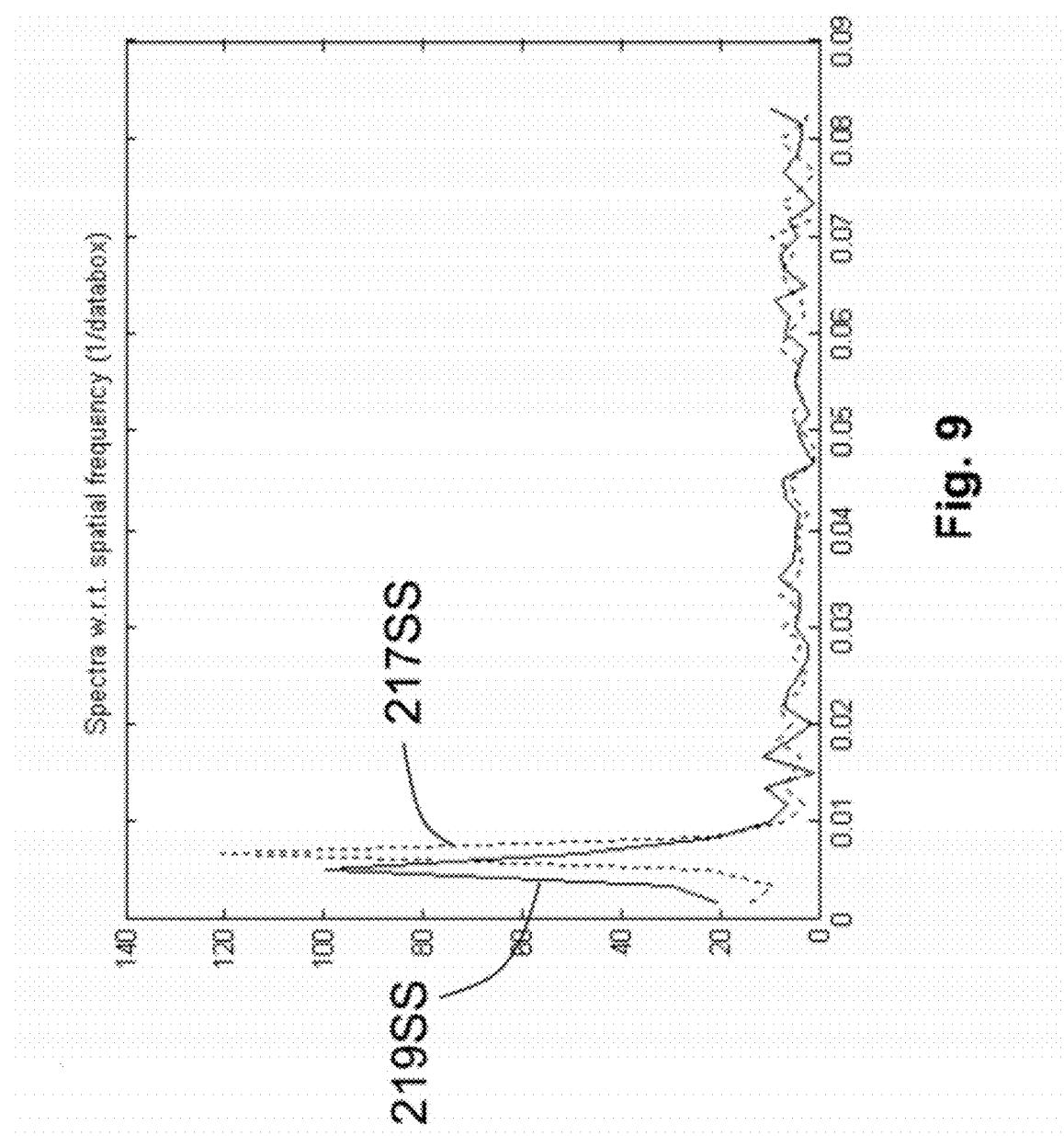
FIG. 9 is the spatial spectra of the scan measurements of FIG. 8.

Scan measurements 210S, 212S (shown as solid lines) and 214S, 216S (shown as dotted lines) obtained from FIG. 7 with two different scan speeds and their spatial spectra are plotted in FIG. 8 and FIG. 9, respectively. The dominant MD spatial spectral components 217SS, 219SS from the spectra, shown as dotted and solid lines, respectively, appear at different spatial frequencies of 0.0053 and 0.0067 (1/databox).

Figure 10:
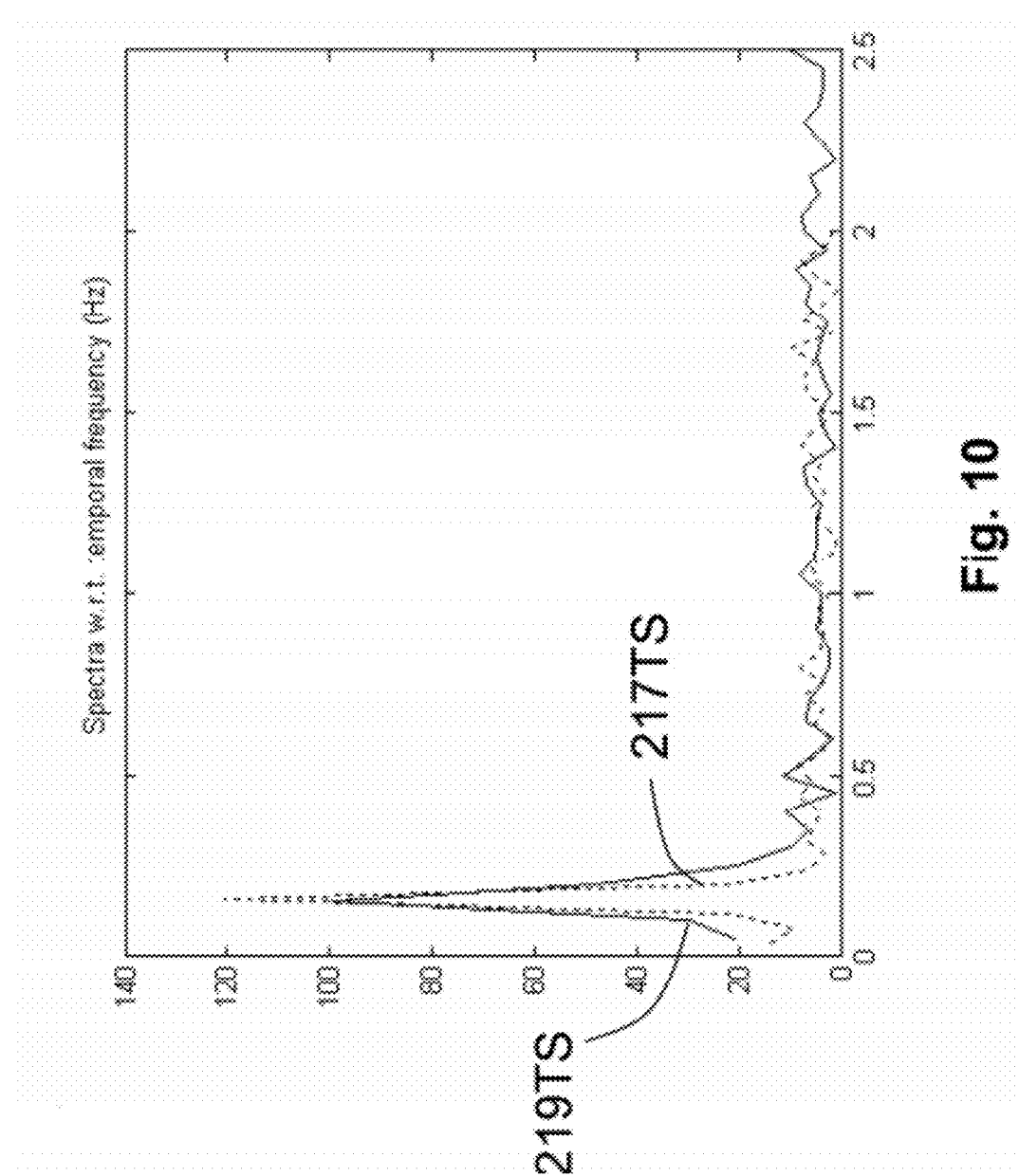
FIG. 10 is the spatial spectra of FIG. 9 converted to temporal frequencies using the measurement scan speeds.

However, by converting the dominant MD spectral components 217SS, 219SS from the spatial spectra to temporal frequencies using their corresponding scan speeds as described earlier, the dominant MD spectral components 217TS, 219TS appear at the same temporal frequency of 0.16 Hz as shown in FIG. 10 as dotted and solid lines, respectively.

Figure 11:
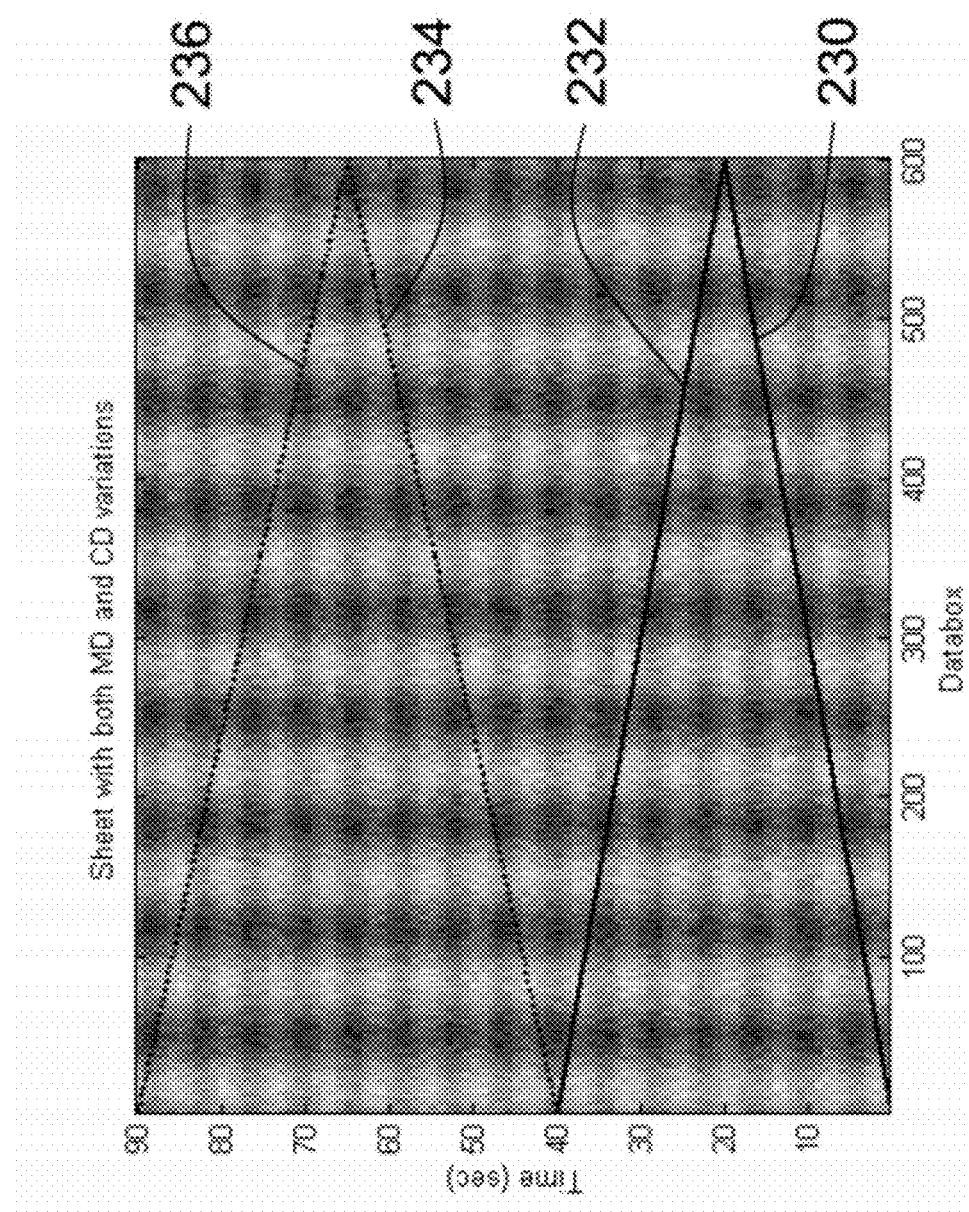
FIG. 11 is a simulated sheet of material with both MD and CD variations and the traces of scans made using two different scan speeds.

The third simulated example is one where the sheet has both MD and CD variations and again two different scan speeds are used (20 second scans and 25 second scans—for 600 databox spatial resolution, these scan speeds correspond to 30 databoxes/sec and 24 databoxes/sec, respectively). A sheet with both MD and CD variations and the traces of scans made using two scan speeds are shown in FIG. 11.

The trace of each scan speed is marked with a diagonal line—the bottom or first two scans 230, 232 (solid lines) are 20 second scans and the two top or last two scans 234, 236 (dotted lines) are 25 second scans. Scan measurements 230S, 232S (solid lines) and 234S, 236S (dotted lines) obtained from FIG. 11 with two different scan speeds and their spatial spectra are plotted in FIG. 12 and FIG. 13, respectively. The dominant CD spectral components 237SS, 239SS, shown as dotted and solid lines, respectively, from the spectra appear at the same spatial frequency of 0.015 (1/databox). The dominant MD spatial spectral components 237'SS, 239'SS from the spectra, shown as dotted and solid lines, respectively, appear at different spatial frequencies of 0.0053 and 0.0067 (1/databox).

Figure 14:
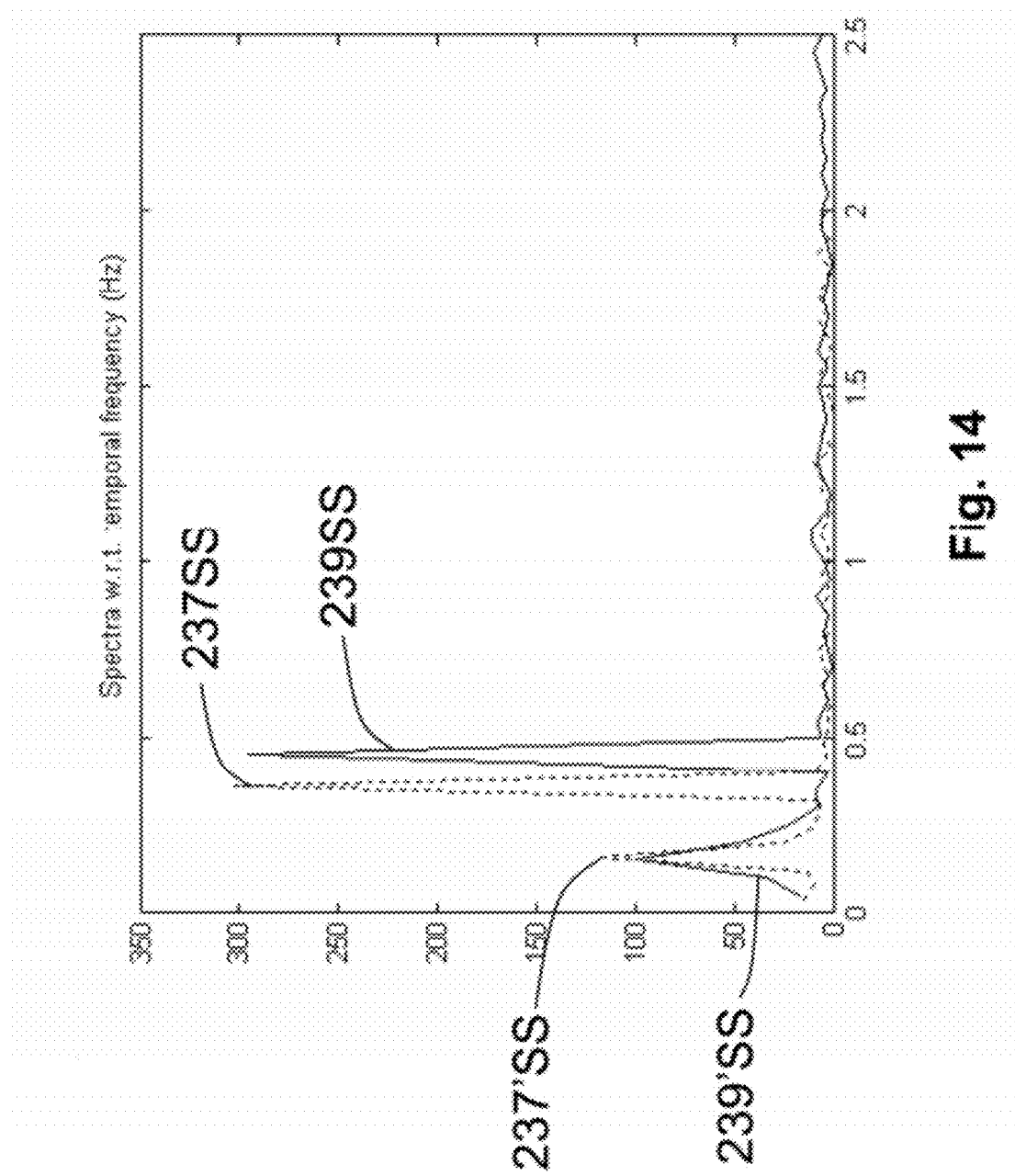
FIG. 14 is the spatial spectra of FIG. 13 converted to temporal frequencies using the measurement scan speeds.

When the dominant CD and MD spectral components 237SS, 239SS, 237'SS, 239'SS are converted to temporal frequencies using their corresponding scan speeds as described earlier, the MD dominant spectral components 237'SS (dotted line), 239'SS (solid line) appear at the same temporal frequency of 0.16 Hz, and the CD spectral components 237SS (dotted line) and 239SS (solid line) appear at different temporal frequencies of 0.36 Hz and 0.45 Hz as shown in FIG. 14.

Thus, when the spectra of scan measurements obtained from different scan speeds are shown with respect to the spatial frequencies (FIG. 13), the dominant spectral components that appear at the same spatial frequency represent the CD variation components. Similarly, when the spectra of scan measurements obtained from different scan speeds are shown with respect to their corresponding temporal frequencies (FIG. 14), the dominant spectral components that appear at the same temporal frequency represent the MD variation components. This result allows effective identification and separation of the CD and MD variations from sheet scan measurements that consist of both CD and MD variations.

Figure 12:
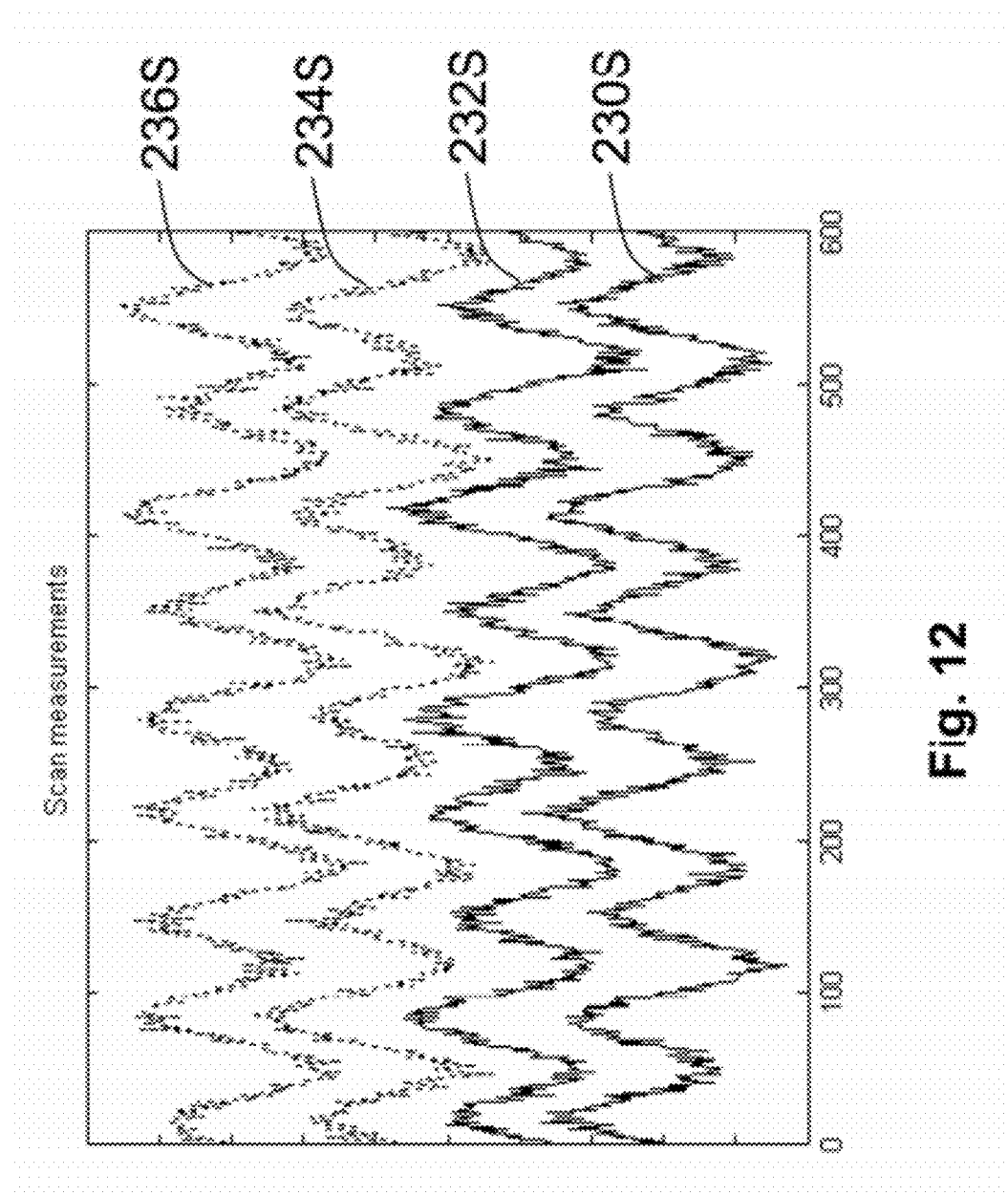
FIG. 12 shows scan measurements of the simulated sheet of FIG. 7 obtained using the scans shown in FIG. 7 having two different scan speeds.
Figure 13:
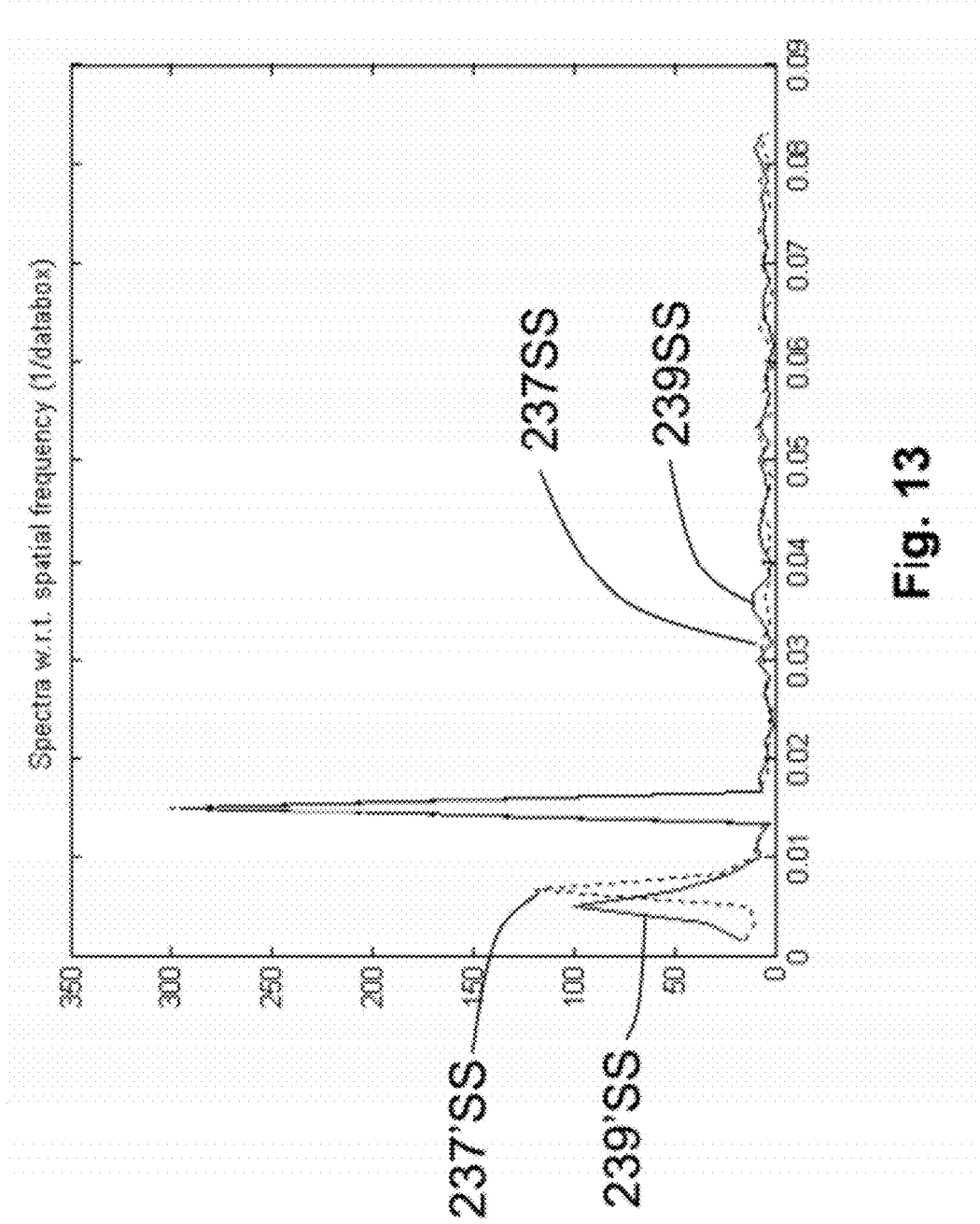
FIG. 13 is the spatial spectra of the scan measurements of FIG. 12.
Figure 15:
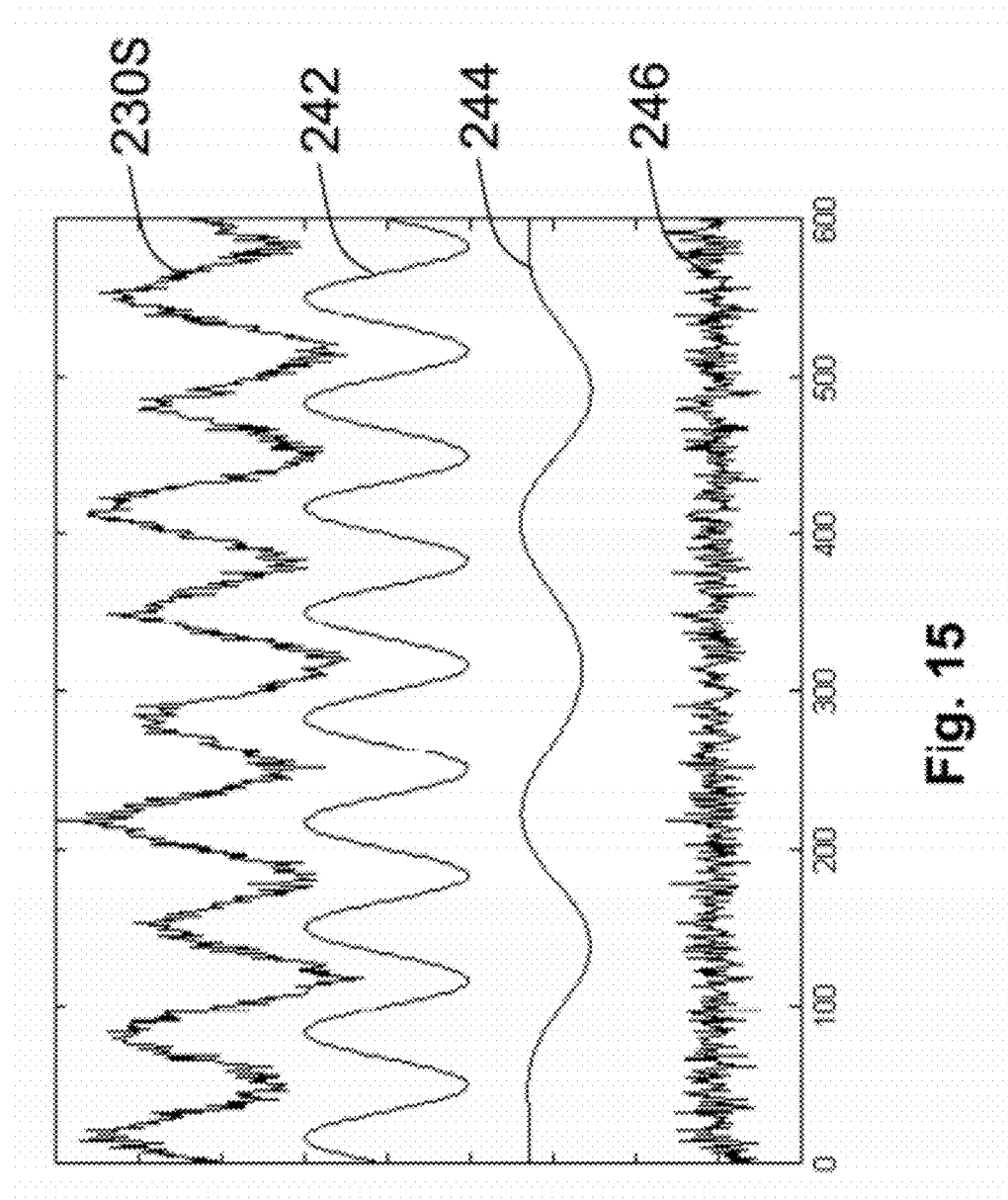
FIG. 15 illustrates a scan measurement, the CD and MD variations in the scan measurement determined using the process of the present application and the background random noise in the scan measurement found by removing the CD and MD variations from the scan measurement.

For example, once the scan measurements of FIG. 12 have been processed as described above to identify the CD and MD variation components in the spectral domain, those variation components can be inverse transformed into the CD variations 242 and the MD variations 244 shown in FIG. 15. The CD variations 242 and the MD variations 244 can then be removed from the scan measurement, for example the scan measurement 230S shown in FIG. 15, to obtain the background random noise 246 in the scan measurement 230S. The CD variations 242 can be used as inputs to a CD controller and the MD variations 244 can be used as inputs to an MD controller to better control processes being measured. The frequencies of the separated CD and MD variations 242, 244 can also be used to determine the root causes of those variations so that the causes can be addressed and thereby those variations eliminated or substantially reduced.

As noted earlier, a process for extracting dominant spectra from a noisy measurement will now be described. In many real world applications, a measurement typically contains both a useful signal and background random noise. For practical purposes, there is always a strong need to separate the useful signal from its background random noise. The challenge is that it is not obvious how to distinguish between the useful signal and the background noise directly from the measurement itself. In practice, very often a measurement can be transformed into the spectral domain using, for example, Fourier transformation to facilitate differentiation between the signal and the background noise. In the spectral domain, the useful signal of the original measurement often shows up as a set of dominant spectra in the power spectrum. A novel process for effectively extracting the dominant spectra from the power spectrum of a given measurement which can be used in the system for determination of CD and/or MD variations from scanning measurements of a sheet of material of the present application will now be described.

The dominant spectra extraction process can be used when working with a variety of measurements including without limitation measurements taken by industrial instrumentation, research laboratory apparatus, medical equipment, communication equipment, and measurements of commercial numerical trends, any historical data series and all forms of multi-dimensional arrays of data. Wherever the measurements are taken and to whatever the measurements apply, the disclosed process effectively identifies/separates the dominant spectral components in the measurements from their background random noise. The extracted dominant spectral components are noise-free and can be used to determine the root causes of the dominant spectra or to reconstruct the dominant variations that are hidden in the measurements as described above with regard to FIG. 15.

Power spectrum analysis is a well-known tool to analyze the spectral contents of measurements. If a measurement contains only random noise, then its power spectrum should have uniform magnitudes at all frequencies. If the spectrum is non-uniform, then there must be a few spectral components larger than the rest. These larger spectral components are the "dominant spectra" in the given measurement and they often represent the useful signal in the given measurement. To separate the dominant spectra, you need to know the magnitude of the noise accurately. However, the magnitude of the noise cannot be accurately estimated if the dominant spectra are not separated from the measurement. Thus, a catch-22 situation is the result.

Although it may be relatively easy to "visually" pick out the dominant spectra from a power spectrum of a measurement, it is not straightforward for an instrument or a computer to systematically pick out the dominant spectra. The dominant spectra can occur at any frequency and have various magnitudes. It is non-trivial to separate dominant spectra from a signal's background random noise. This aspect of the present application overcomes these problems and enables machine extraction of the dominant spectra from a spectrum of a measurement using estimation and threshold setting techniques.

Figure 16:
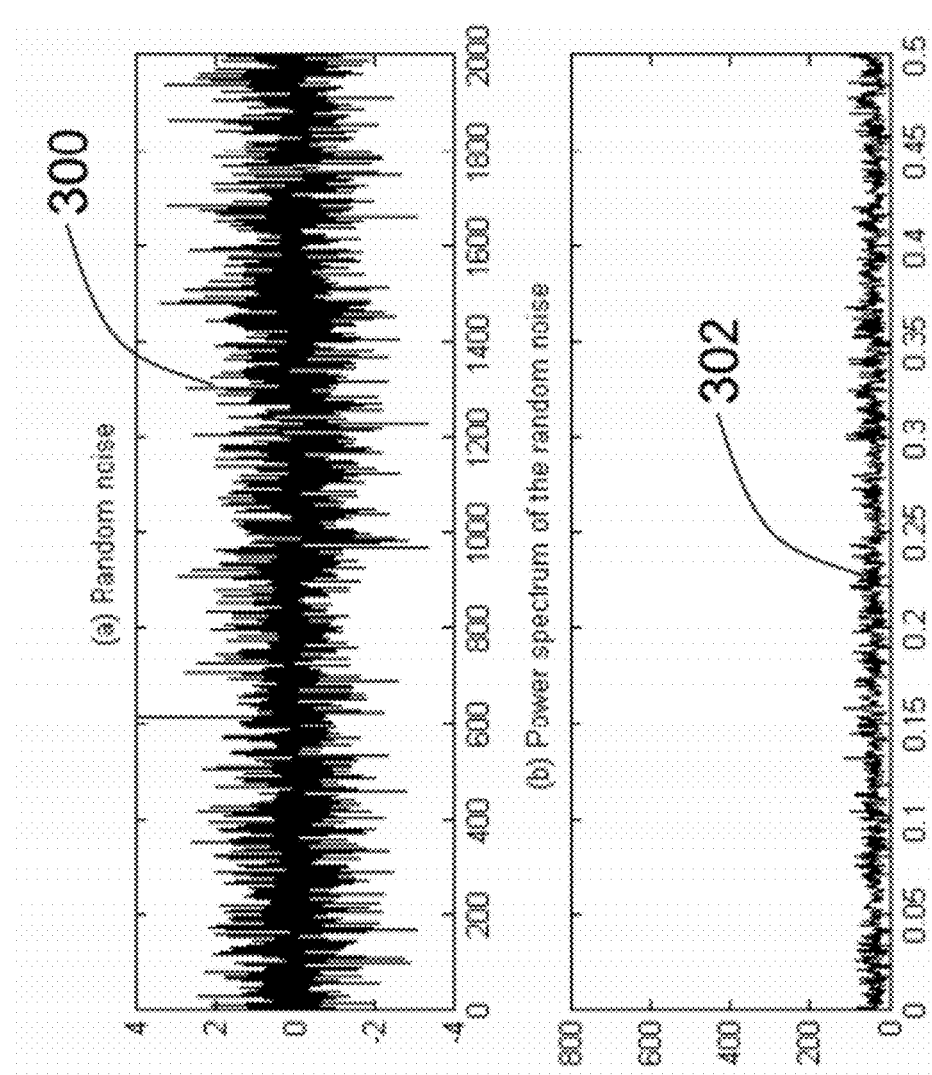
FIG. 16($a$) illustrates a measurement that contains only random noise.

Given a measurement as a sequence of sampled data, the power spectrum of the measurement can be obtained using a Fast Fourier Transformation (FFT) or Discrete Fourier Transformation (DFT) algorithm. If the measurement 300 contains only random noise as shown in FIG. 16(*a*), then its derived power spectrum 302 is substantially uniform across its entire frequency range as shown in FIG. 16(*b*).

Figure 17:
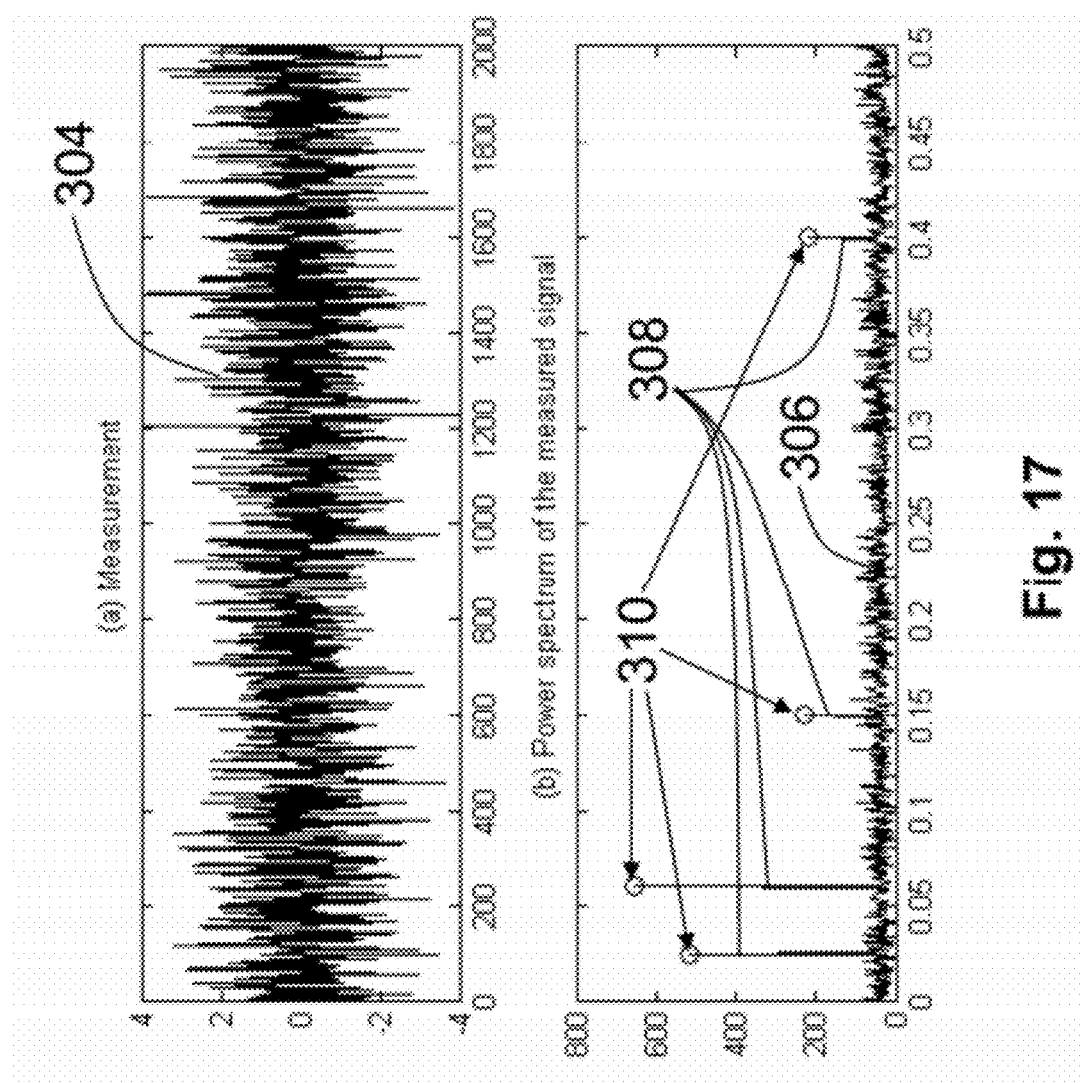
FIG. 17($a$) illustrates a measurement that contains specific signals (or variations) at several frequencies and background random noise.

If the measurement 304 contains specific signals (or variations) at several frequencies as shown in FIG. 17(*a*), its power spectrum 306 as seen in FIG. 17(*b*) will show spikes 308 at those frequencies. The spectral components which are larger than the rest and marked with circles 310 in FIG. 17(*b*) are the "dominant spectra" of the signals in the measurement. These "dominate spectra" can be systematically extracted using the process for extracting dominant spectra from a noisy measurement in accordance with this present aspect of the present application.

An example of a series of operations that can be performed for extraction of dominant spectra or spectral components from measurements will now be described followed by an example illustrating the basic principles used in the present application to ensure complete understanding of operation of the dominant spectra extraction process of the present application.

1. Sort all spectral components from the original power spectrum in order of their magnitudes and keep their sorting order.
2. Approximate the background noise of the sorted spectrum with a first polynomial, typically a low order polynomial.
3. Identify the outlier spectral components that significantly deviate from the first low-order polynomial.
4. Remove the outlier spectral components identified in operation 3 from the original power spectrum. The remaining spectral components represent the background noise of the original power spectrum.
5. Approximate the remaining spectral components from operation 4 representative of the background noise of the original power spectrum with a second polynomial, typically a low order polynomial.
6. Extract the spectral components that significantly deviate from the second polynomial, typically a low-order polynomial. The extracted spectral components are the dominant spectral components of the original power spectrum.

Figure 18:
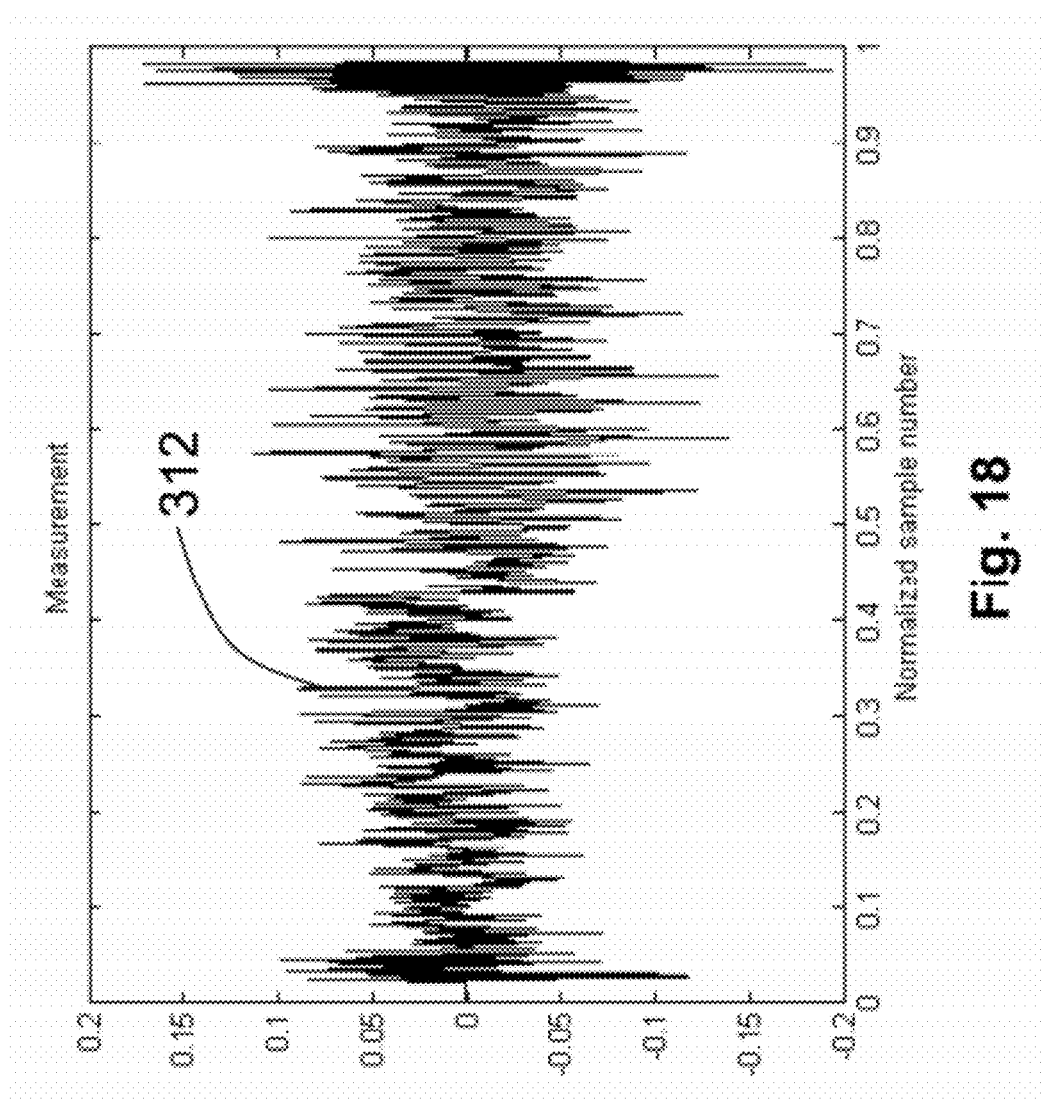
FIG. 18 illustrates a measurement which may contain a few dominant spectra.

An example for extraction of dominant spectra or spectral components from actual measurements makes reference to FIG. 18 which illustrates a measurement 312 which may contain a few dominant spectra.

Figure 19:
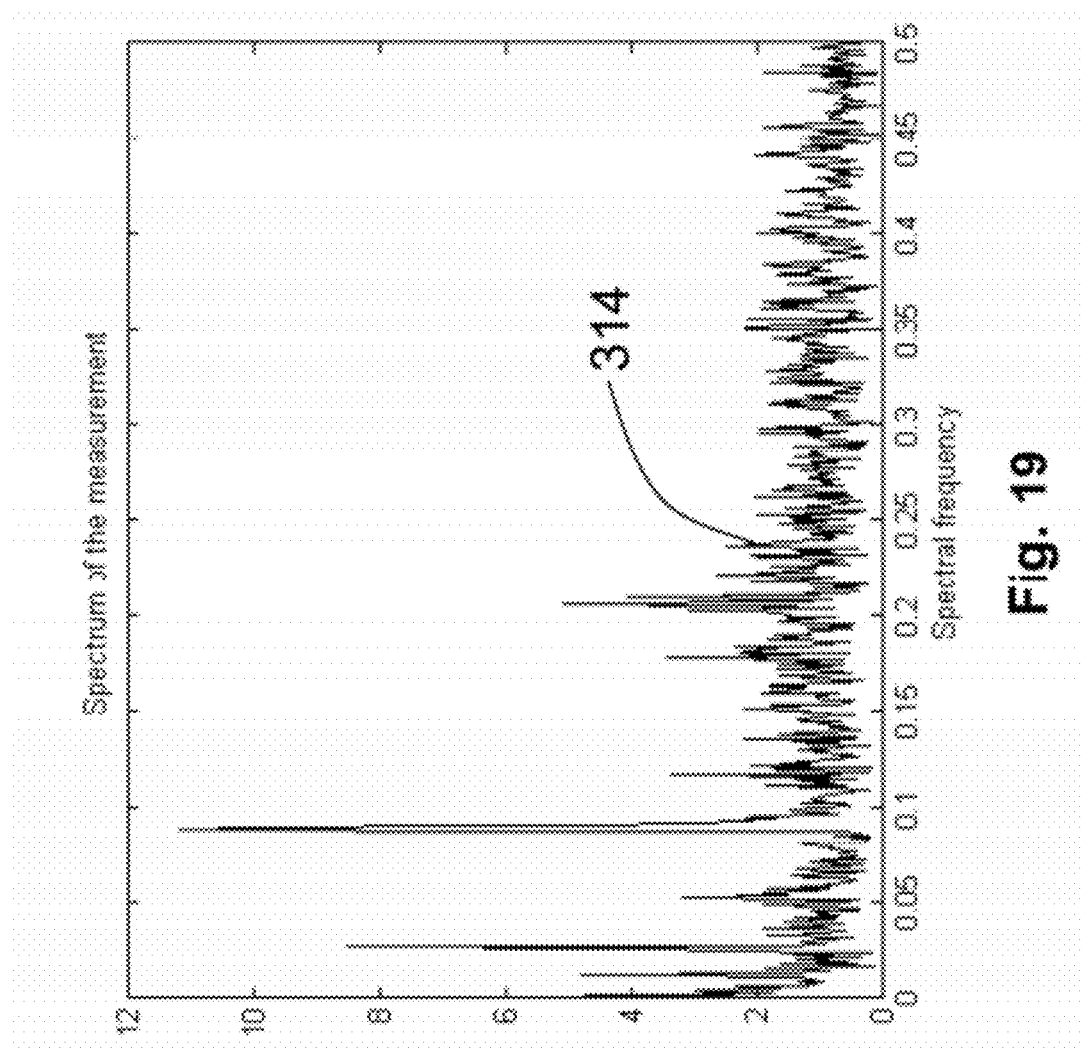
FIG. 19 illustrates the power spectrum of the measurement of FIG. 18.

FIG. 19 illustrates the power spectrum 314 of the measurement 312 shown in FIG. 18. Even though a few dominant spectra are visually noticeable in FIG. 19, it is non-trivial to consistently identify all dominant spectra that meet desired criteria from a power spectrum of measurements. One simple approach that might be used is to set a uniform threshold across the entire spectrum. Unfortunately, such a uniform threshold would not work well because background random noise could have slightly higher spectra near the low frequency range.

Figure 20:
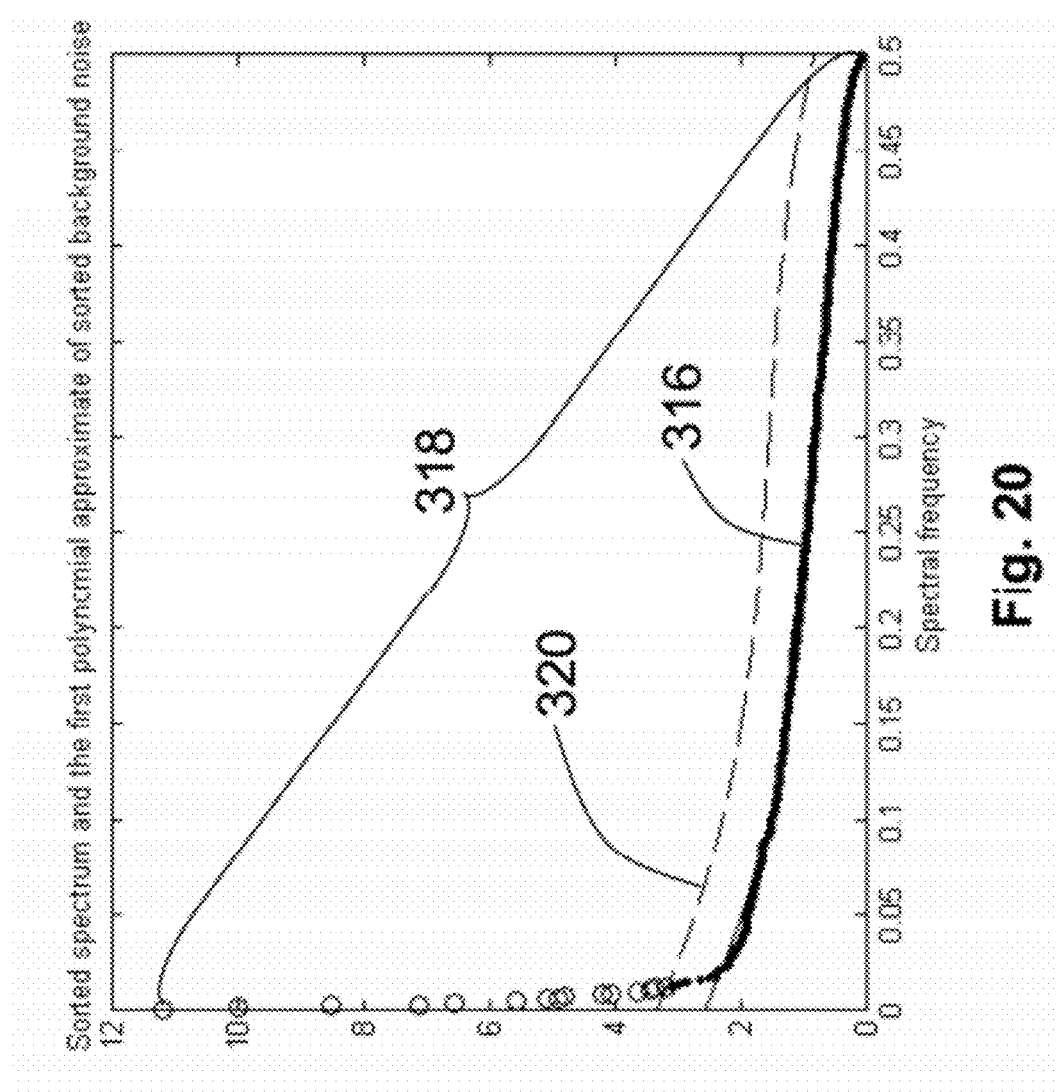
FIG. 20 shows the spectral components of power spectrum of FIG. 19 that have been sorted and placed in descending order based on their magnitudes.

FIG. 20 shows the spectral components of FIG. 19 that have been sorted and placed in descending order based on their magnitudes. The generally flat region 316 of the resulting ordered spectrum 318, approximately from spectral frequency 0.05 to spectral frequency 0.5 of FIG. 20, is the region of the spectrum that represents background noise of the measurement and that generally flat region is approximated using a low-order first polynomial. A first threshold is set relative to the first polynomial as shown by the dashed line 320. The first threshold can be set by selecting a distance from the first polynomial, for example set in relation to the standard deviation $\sigma_1$ of the statistical distribution of the spectral components that comprise the generally flat region of the ordered spectrum of FIG. 20 with respect to their corresponding first polynomial reference. Currently, it is believed that the first threshold could be within a range of about $5\sigma_1$ to $10\sigma_1$. The outlier spectra that significantly deviate from the first polynomial and exceed the first threshold (shown as circles in FIG. 20) include the dominant spectral components of the power spectrum and are removed from the ordered spectrum to form a noise spectrum.

Figure 21:
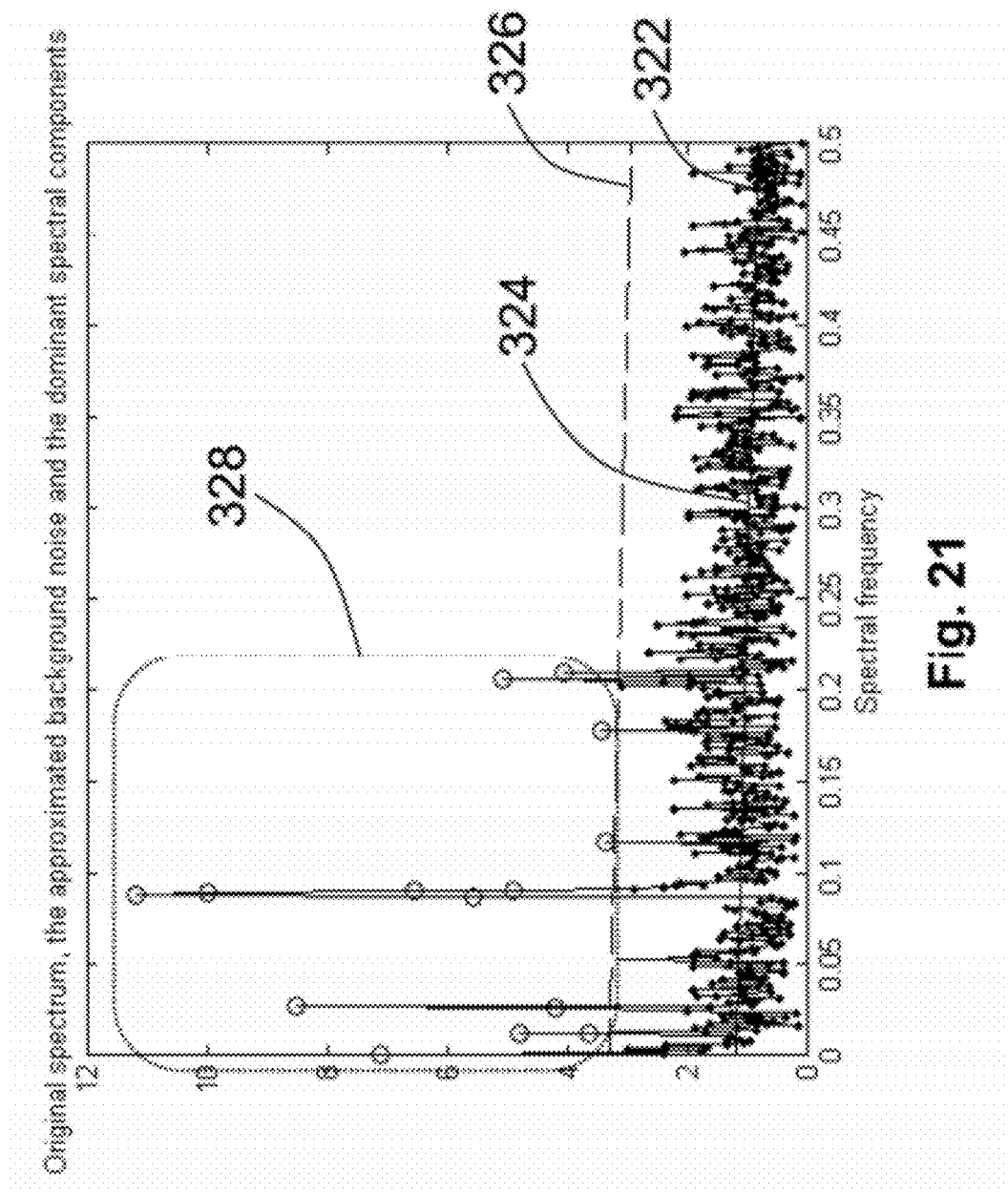
FIG. 21 illustrates a noise spectrum determined from the ordered power spectrum of FIG. 20 and dominant spectral components of the power spectrum of the measurement of FIG. 18 determined in accordance with one aspect of the present application.

The noise spectrum 322, shown as dots in FIG. 21, is used to approximate the background noise in the original power spectrum 314. As is typical, a low-order second polynomial 324 approximation is made of the noise spectrum shown in FIG. 21. A second threshold 326 is set relative to the second polynomial 324 as shown by the dashed line 326 in FIG. 21. The second threshold 326 can be set by selecting a distance from the second polynomial 324, for example the second threshold 326 can be set according to the statistical distribution of the background noise approximated by the noise spectrum 322. The dashed line 326 in FIG. 21 is set at three times the standard deviation, $3\sigma_2$, of the background noise with respect to the second polynomial 324. The second threshold 326 can be adjusted to provide the best results for the dominant spectra extraction process of the present application. Currently, it is believed that the second threshold could be within a range of about $3\sigma_2$ to $6\sigma_2$.

In FIG. 21, the spectra (represented by circles within the dotted line 328) which are above the dashed threshold 326 so that they deviate significantly from the background noise or noise spectrum 322 are identified as the dominant spectra within the power spectrum.

The selection of the first and second polynomials and the first and second thresholds provide tuning parameters for the dominant spectra extraction process of the present application.

The dominant spectra extraction process of the present application can be used in many different applications. For example, if the original measurement is a flow rate of a pipe in a chemical plant, the frequency of an extracted dominant spectral component might be matched to an oscillation frequency of a control valve so that an alarm can be given to check the control valve so see whether it may be malfunctioning and in need of repair or replacement.

If the original measurement consists of multiple dominant spectral components, for example as shown in FIG. 21, the dominant spectra extraction process of the present application can be used to extract them all so that they can be used to trace each individual dominant spectral component to its root-cause. The root causes can be a number of different valves, pumps, other rotating devices and the like.

When dominant spectra are extracted using the disclosed dominant spectra extraction process of the present application, they can be used to reconstruct their original signals by applying inverse transformations, such as inverse Fourier transformation, to the dominant spectra. The resulting reconstructed signals can be used for control or for estimating potential improvement if the dominant spectra are eliminated.

The disclosed processes are easy to use and very effective at picking out the dominant spectra systematically for a wide variety of measurements.

Although the invention of the present application has been described with particular reference to certain illustrated embodiments thereof, variations and modifications of the present invention can be effected within the spirit and scope of the following claims.

For example, the disclosed process for determining CD and/or MD variations from scan measurements of a sheet of material can be applied to a single scanner frame that scans at two or more scanning speeds, two or multiple scanner frames that scan at different scanning speeds where each scanner frame hosts a similar sensor, or two or multiple frames that scan at two or multiple scanning speeds on each frame. Temporal resolution (number of samples per second) and/or spatial resolution (number of databoxes) from each sensor on each frame does not have to be the same. In reality, the spatial resolution is set to be the same to keep the system simpler. The disclosed process does not always have to be applied to entire scan measurements. Rather, this process can be applied to any portion of the scan measurements. If the disclosed process is applied to a sensor that scans at two or multiple scanning speeds, the order of the scanning speeds can be arranged in many different ways in addition to those illustrated in FIGS. 2(a), 2(b) and 2(c) which show three different examples: V1, V1, V2, V2, V1, V1 . . . (block); V1, V2, V1, V2, V1 . . . (alternating); and V1, V2, V1, V1, V2, V1, V2, V2 . . . (random). The power spectra of scan measurements can be updated or accumulated with the scan measurements of the same scanning speed either regularly, intermittently or in a batch. The process of determining MD and CD spectral components and frequencies does not have to be fully synchronized with the update of the scan measurements or the separation of MD and CD variations from scan measurements. However, the determination of MD and CD frequencies is needed before the inverse transformation can be applied to separate MD and CD variations. The determination of MD and/or CD spectral components can be triggered by events or executed periodically by measurement updates but the actual separation of CD and MD variations from the scan measurements most likely will be executed regularly whenever scan measurements are updated.

What is claimed is:

1. A process for determining CD variations from scanning measurements made of a sheet of material comprising:
   scanning at least one sensor over a moving sheet of material to be measured at a first scanning speed to generate first scan measurements, the at least one sensor moving transversely relative to the moving sheet of material, the first scan measurements including mixed CD-MD variations of the sheet of material;
   transforming said first scan measurements into a first spatial power spectrum with respect to a first spatial frequency;
   detecting first spatial dominant spectral components of said first spatial power spectrum;
   scanning at least one sensor over said moving sheet of material to be measured at a second scanning speed to generate second scan measurements, the at least one sensor moving transversely relative to the moving sheet of material, the second scan measurements including mixed CD-MD variations of the sheet of material;
   transforming said second scan measurements into a second spatial power spectrum with respect to a second spatial frequency;
   detecting second spatial dominant spectral components of said second spatial power spectrum; and
   identifying CD spectral components of the scanning measurements by determining at least one of said first spatial dominant spectral components that are at the same spatial frequency as at least one of said second spatial dominant spectral components, the CD spectral components representing the CD variations separated from the mixed CD-MD variations of the sheet of material, the CD variations including a plurality of values over a CD range of the sheet of material.

2. The process as claimed in claim 1 further comprising:
   scanning at least one sensor over a sheet of material to be measured at a third scanning speed to generate third scan measurements;
   transforming said third scan measurements into a third spatial power spectrum with respect to a third spatial frequency;
   detecting third spatial dominant spectral components of said third spatial power spectrum; and
   identifying CD spectral components of the scanning measurements by determining at least one of said first spatial dominant spectral components that are at the same spatial frequency as at least one of said second spatial dominant spectral components and at least one of said third spatial dominant spectral components.

3. The process as claimed in claim 1 further comprising constructing the CD variations within said scanning measurements by inverse transformation of said CD spectral components.

4. The process as claimed in claim 1 wherein the step of detecting first spatial dominant spectral components of said first spatial power spectrum comprises:
   sorting all spectral components from said first spatial power spectrum in order of magnitude to form a first ordered spatial power spectrum;
   representing background noise of said first ordered spatial power spectrum with a first polynomial;
   setting a first deviation threshold with respect to said first polynomial;
   comparing spectral components of said first ordered spatial power spectrum to said first deviation threshold;
   removing spectral components of said first ordered spatial power spectrum that exceed said first deviation threshold from said first ordered spatial power spectrum to form a first noise spatial power spectrum;
   representing said first noise spatial power spectrum in said first spatial power spectrum with a second polynomial;
   setting a second deviation threshold with respect to said second polynomial; and identifying spectral components of said first spatial power spectrum that exceed said second deviation threshold as first spatial dominant spectral components of said first spatial power spectrum.

5. The process as claimed in claim 1 wherein the step of detecting second spatial dominant spectral components of said second spatial power spectrum comprises:
sorting all spectral components from said second spatial power spectrum in order of their magnitudes to form a second ordered spatial power spectrum;
representing background noise of said second ordered spatial power spectrum with a third polynomial;
setting a third deviation threshold with respect to said third polynomial;
comparing spectral components of said second ordered spatial power spectrum to said third deviation threshold;
removing spectral components of said second ordered spatial power spectrum that exceed said third deviation threshold from said second spatial power spectrum to form a second noise spatial power spectrum;
representing said second noise spatial power spectrum with a fourth polynomial;
setting a fourth deviation threshold with respect to said fourth polynomial; and
identifying spectral components of said second spatial power spectrum that exceed said fourth deviation threshold as second spatial dominant spectral components of said second spatial power spectrum.

6. The process as claimed in claim 1 further comprising:
transforming said first scan measurements into a first temporal power spectrum with respect to a first temporal frequency;
detecting first temporal dominant spectral components of said first temporal power spectrum;
transforming said second scan measurements into a second temporal power spectrum with respect to a second temporal frequency;
detecting second temporal dominant spectral components of said second temporal power spectrum; and
identifying MD spectral components of said scanning measurements by determining at least one of said first temporal dominant spectral components at the same temporal frequency as at least one of said second temporal dominant spectral components, the MD spectral components representing the MD variations separated from the mixed CD-MD variations of the sheet of material, the MD variations including a plurality of values over an MD range of the sheet of material.

7. The process as claimed in claim 6 further comprising:
constructing the CD variations within said scanning measurements by inverse transformation of said CD spectral components, and;
constructing the MD variations within said scanning measurements by inverse transformation of said MD spectral components.

8. A process for determining MD variations from scanning measurements made of a sheet of material comprising:
scanning at least one sensor over a moving sheet of material to be measured at a first scanning speed to generate first scan measurements, the at least one sensor moving transversely relative to the moving sheet of material, the first scan measurements including mixed CD-MD variations of the sheet of material;
transforming said first scan measurements into a first temporal power spectrum with respect to a first temporal frequency;
detecting first temporal dominant spectral components of said first temporal power spectrum;
scanning at least one sensor over said sheet of material to be measured at a second scanning speed to generate second scan measurements, the at least one sensor moving transversely relative to the moving sheet of material, the second scan measurements including mixed CD-MD variations of the sheet of material;
transforming said second scan measurements into a second temporal power spectrum with respect to a second temporal scanning frequency;
detecting second dominant spectral components of said second temporal power spectrum; and
identifying MD spectral components of said scanning measurements by determining at least one of said first temporal dominant spectral components that is at the same temporal frequency as at least one of said second temporal dominant spectral components, the MD spectral components representing the MD variations separated from the mixed CD-MD variations of the sheet of material, the MD variations including a plurality of values over an MD range of the sheet of material.

9. The process as claimed in claim 8 further comprising constructing the MD variations within said scanning measurements by inverse transformation of said MD spectral components.

10. The process as claimed in claim 8 further comprising:
transforming said first scan measurements into a first spatial power spectrum with respect to a first spatial frequency;
detecting first spatial dominant spectral components of said first spatial power spectrum;
transforming said second scan measurements into a second spatial power spectrum with respect to a second spatial frequency;
detecting second spatial dominant spectral components of said second spatial power spectrum; and
identifying CD spectral components of said scanning measurements by determining at least one of said first spatial dominant spectral components that is at the same spatial frequency as at least one of said second spatial dominant spectral components.

11. The process as claimed in claim 10 further comprising:
constructing the MD variations within said scanning measurements by inverse transformation of said MD spectral components; and
constructing the CD variations within said scanning measurements by inverse transformation of said CD spectral components.

* * * * *